United States Patent [19]
Hubbell et al.

[11] Patent Number: 6,153,743
[45] Date of Patent: Nov. 28, 2000

[54] LITHOGRAPHIC MASK DESIGN AND SYNTHESIS OF DIVERSE PROBES ON A SUBSTRATE

[75] Inventors: Earl A. Hubbell, Los Angeles; Lubert Stryer, Stanford, both of Calif.

[73] Assignee: Affymetrix, Inc., Santa Clara, Calif.

[21] Appl. No.: 09/059,779

[22] Filed: Apr. 13, 1998

Related U.S. Application Data

[63] Continuation-in-part of application No. 08/767,892, Dec. 17, 1996, abandoned.

[51] Int. Cl.⁷ .................................................. C07H 21/00
[52] U.S. Cl. ...................... 536/25.3; 530/335; 530/334; 530/333
[58] Field of Search ........................ 536/25.3; 530/335, 530/334, 333

[56] References Cited

U.S. PATENT DOCUMENTS

| | | | |
|---|---|---|---|
| 5,143,854 | 9/1992 | Pirrung et al. | 436/518 |
| 5,235,626 | 8/1993 | Flamholz et al. | 378/34 |
| 5,384,261 | 1/1995 | Winkler et al. | 436/518 |
| 5,424,186 | 6/1995 | Fodor et al. | 435/6 |
| 5,460,908 | 10/1995 | Reinberg | 430/5 |
| 5,527,681 | 6/1996 | Holmes | 435/6 |

FOREIGN PATENT DOCUMENTS

| | | |
|---|---|---|
| 95/11995 | 5/1995 | WIPO . |

OTHER PUBLICATIONS

Fodor et al., "Light–Directed, Spatially Addressable Parallel Chemical Synthesis," Feb. 15, 1991, Research Article.

Brown et al., "An Inexpensive MSI/LSI Mask Making System," IEEE Symposium Proceedings 1981, University Government Industry Microelectronics, Sponsored by IEEE, Starkville, Mississippi, pp. III–31 to III–38.

Southern, E. M., "Analyzing and Comparing Nucleic Acid Sequences by Hybridization to Arrays of Oligonucleotides: Evaluation Using Experimental Models," Genomics, 13, 1992, pp. 1008–1017.

Ed M. Southern, "DNA Chips: Analysing Sequence by Hybridization to Oligonucleotides on a Large Scale," TIG, Mar. 1996, vol. 12, No. 3, pp. 110–115.

*Primary Examiner*—Keith D. MacMillan
*Assistant Examiner*—T. D. Wessendorf
*Attorney, Agent, or Firm*—Ritter, Van Pelt & Yi LLP

[57] ABSTRACT

Systems and methods of synthesizing probes on a substrate are provided. One or more shift reticles are utilized to uniformly add monomers to the substrate at specified locations. The shift reticles are shifted relative to the substrate between monomer addition steps. Additionally, characteristics of the desired probes may be specified at synthesis time.

25 Claims, 28 Drawing Sheets

Microfiche Appendix Included
(1 Microfiche, 72 Pages)

TARGET SEQUENCE: TGACAT
3-MER PROBES (COMPLEMENTS)

| ACT | CTG | TGT | GTA |

|         |      |      |      |      |
|---------|------|------|------|------|
| A-LANE  | A<u>A</u>T | C<u>A</u>G | T<u>A</u>A | G<u>A</u>A |
| C-LANE  | A<u>C</u>T* | C<u>C</u>G | T<u>C</u>T | G<u>C</u>A |
| T-LANE  | A<u>T</u>T | C<u>T</u>G* | T<u>T</u>T | G<u>T</u>A* |
| G-LANE  | A<u>G</u>T | C<u>G</u>G | T<u>G</u>T* | G<u>G</u>A |

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO:1:

TACCGTGAAG CTACG                                                              15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:2:

```
ATGGCACTTC GATGC                                               15
```

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:3:

```
ATGGCACGTC GATGC                                               15
```

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:4:

```
ATGGCACCTC GATGC                                               15
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:5:

```
ATGGCACATC GATGC                                               15
```

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:6:

```
ATGGCACTCG ATGC                                                14
```

-continued (2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:7:

AGCGATANCT GCGTA          15

LITHOGRAPHIC MASK DESIGN AND SYNTHESIS OF DIVERSE PROBES ON A SUBSTRATE

This is a continuation-in-part of application Ser. No. 08/767,892, filed Dec. 17, 1996, abandoned, which is hereby incorporated by reference for all purposes.

COPYRIGHT NOTICE

A portion of the disclosure of this patent document contains material that is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

MICROFICHE APPENDIX

A Microfiche Appendix (1 microfiche, 72 frames) of a computer program listing of an embodiment of the invention is included herewith.

BACKGROUND OF THE INVENTION

The present invention is related to computer systems for generating masks. More particularly, the invention provides systems and methods for generating and utilizing masks to form probes on a substrate.

U.S. Pat. No. 5,424,186 describes a pioneering technique for, among other things, forming and using high density arrays of molecules such as oligonucleotide, RNA, peptides, polysaccharides, and other materials. This patent is hereby incorporated by reference for all purposes. Arrays of oligo-nucleotides or peptides, for example, are formed on the surface by sequentially removing a photoremovable group from a surface, coupling a monomer to the exposed region of the surface, and repeating the process. These techniques have been used to form extremely dense arrays of oligonucleotides, peptides, and other materials. Such arrays are useful in, for example, drug development, oligonucleotide sequencing, oligonucleotide sequence checking, and a variety of other applications. The synthesis technology associated with this invention has come to be known as "VLSIPS" or "Very Large Scale Immobilized Polymer Synthesis" technology.

Additional techniques for forming and using such arrays are described in U.S. Pat. No. 5,384,261, which is also incorporated by reference for all purposes. Such techniques include systems for mechanically protecting portions of a substrate (or chip), and selectively deprotecting/coupling materials to the substrate. These techniques are now known as "VLSIPS II." Still further techniques for array synthesis are provided in U.S. application Ser. No. 08/327,512, also incorporated herein by reference for all purposes.

Dense arrays fabricated according to these techniques are used, for example, to screen the array of probes to determine which probe(s) are complementary to a target of interest. According to one specific aspect of the inventions described above, the array is exposed to a labeled target. The target may be labeled with a wide variety of materials, but an exemplary label is a fluorescein label. The array is then scanned with a confocal microscope based detection system, or other related system, to identify where the target has bound to the array. Other labels include, but are not limited to, radioactive labels, large molecule labels, and others.

While meeting with dramatic success, such methods meet with limitations in some circumstances. For example, during the design of the layout of molecules in an array according to the above techniques, it is necessary to design a "mask" that will define the locations on a substrate that are exposed to light. While such masks are easily fabricated, they tend to be costly. The design of such masks is described in U.S. Pat. No. 5,571,639, incorporated herein by reference for all purposes.

Often it is desirable to have a specific layout of molecules in an array for a particular application. For example, PCT WO95/11995, which is incorporated by reference for all purposes, describes the synthesis of particular arrays for use in HIV diagnostics, the diagnosis of genes relevant to certain cancers, evaluation of the mitochondrial oligonucleotide, and other applications. In many of these applications there is demand for a large volume of identical chips, such as in HIV diagnostics. In many situations, the manufacture of a particular probe array will require a mask (or mask set) with as many as one hundred reticles or more. The cost of masks in these situations, while high on a per mask basis, becomes quite small when viewed in light of the number of identical arrays that may be synthesized with a particular mask.

However, in many other applications, such as particular research applications, it is desirable to synthesize a relatively small number of arrays with a particular layout of probes, perhaps as few as a single array. While this is certainly possible and has found wide utility in the art, it is costly to fabricate a single mask (or mask set) for the manufacture of only a few probe arrays. Accordingly, the "per chip" cost of masks in these situations can be quite high (on the order of thousands of dollars).

Accordingly, it is desirable to identify more efficient techniques for designing and using lithographic masks in the manufacture of probe arrays and, in particular, reduce the number of reticles required for a low volume design.

SUMMARY OF THE INVENTION

The present invention provides techniques for more economically synthesizing arrays of probes on a substrate. One or more "shift" reticles are utilized to synthesize many different probe sets on a substrate. A shift reticle is a reticle that is shifted (one position or more) after a monomer addition step and then reused which reduces the number of reticles (or masks) required. Additionally, the shift masks uniformly add monomers to the substrate at certain probe locations during synthesis. Embodiments of the invention allow the length of the probes and interrogation position to be specified at synthesis time thereby providing greater flexibility in chip synthesis.

In one embodiment of the invention, a method of synthesizing probes on a substrate, comprises the steps of: coupling monomers on the substrate at locations specified by at least one shift reticle; shifting the at least one shift reticle relative to the substrate; and after shifting the at least one shift reticle, coupling monomers on the substrate at locations specified by the at least one shift reticle; wherein probes including monomers are synthesized on the substrate.

In another embodiment of the invention, a method of synthesizing probes on a substrate, comprises the steps of: providing at least one reticle, the at least one reticle for uniformly adding monomers to the substrate at specified locations; receiving input as to a characteristic of the probes desired; and utilizing the at least one reticle to synthesize the desired probes on the substrate. The characteristic may be the length of the desired probes, the interrogation position, or the monomer addition order for synthesizing the desired probes.

In another embodiment of the invention, a method of synthesizing probes on a substrate comprises the steps of: providing a set of reticles having monomer addition regions, each reticle for coupling a different type of monomer on the substrate; utilizing each reticle of the set to couple a first layer of monomers on the substrate, the first layer of monomers including different types of monomers; and shifting each reticle of the set relative to the substrate to couple a second layer of monomers on the first layer, the second layer of monomers including different types of monomers; wherein a plurality of probes including two monomers are formed on the substrate.

In another embodiment, a method for determining the layout of a reticle for synthesizing probes on a substrate comprises the steps of: receiving input of a target sequence of monomers; selecting a type of monomer in the target sequence; and designing a reticle with monomer addition regions corresponding to each monomer in the target sequence that is the selected type of monomer.

In another embodiment, a method of synthesizing probes on a substrate comprises the steps of: coupling a plurality of first monomers on the substrate at locations specified by a set of monomer addition regions of a reticle; shifting the reticle relative to the substrate; and coupling at least one second monomer on one of the first monomers at a location specified by one of the set of monomer addition regions of the reticle; wherein a probe including the first and second monomers is formed on the substrate.

In another embodiment, a computer-implemented method for determining the layout of a reticle for synthesizing probes on a substrate comprises the steps of: receiving input of a target sequence of monomers; selecting a type of monomer in the target sequence; and designing a reticle with monomer addition regions specified by $$n*(i-1)+1$$

wherein n= the number of different types of monomers and i= a position of a first monomer in the target sequence.

In another embodiment, a method for specifying the layout of a substrate including probes synthesized on the substrate, comprises the steps of: defining the probes to be synthesized on the substrate as a sequential list of analysis regions, each analysis region including probes; receiving input as to a characteristic of the sequential list of analysis regions; and designing at least one reticle to synthesize the probes of each analysis region on the substrate with the input characteristic. Typically the input characteristic includes the location, scale or orientation of the analysis regions.

In another embodiment, a method of synthesizing rows of probes including an interrogation position on a substrate, comprising the steps of: coupling non-interrogation position monomers on the substrate in a first region having a first width; and coupling rows of interrogation position monomers on the substrate in a second region having a second width, the second region being within the first region and the second width being less than the first width. Hybridization data from the probes may be more accurate because the "edge effect" between adjacent probe regions or cells is reduced.

In other embodiments, shift masks may be utilized to synthesize diverse probes for interrogating a base position in a target. For example, probes of a specific length may be synthesized that include every possible interrogation position in the probes. Additionally, probes of different lengths with different interrogation positions may be synthesized on a chip at the same time.

A further understanding of the nature and advantages of the inventions herein may be realized by reference to the remaining portions of the specification and the attached drawings.

BRIEF DESCRIPTION OF THE DRAWINGS

FIG. 11B shows probes on a chip that vary at an interrogation position.

FIG. 12B shows probes on a chip that vary at an interrogation position.

DETAILED DESCRIPTION OF PREFERRED EMBODIMENTS

Terminology

As used herein, the following terms are intended to have the following meanings:

"Mask" refers to a lithographic member, usually a plate of glass, with a number of apertures therein that allow for selective passage of light. A mask may contain one or more reticles.

"Reticle" refers to all or a particular portion of a mask that is used to direct light to a substrate during an exposure.

Introduction

High density, miniaturized arrays of molecular probes are made herein using light directed synthesis techniques. Such arrays may be arrays of oligonucleotides, peptides, small molecules (such as benzodiazapines, prostoglandins, beta-turn mimetics), non-natural ligands, enzymes, or any of a wide variety of other molecules synthesized in a "building block" fashion, such as oligosaccharides, and the like. Oligonucleotide probe arrays are representative of the arrays that may be used according to specific aspects of the invention herein.

The design and fabrication of oligonucleotide probe arrays relies on VLSIPS technology according to a specific aspect of the invention. The first step in fabricating a oligonucleotide probe array involves choosing a set of oligonucleotide probes to be synthesized on the chip. Suppose, for example, it is desirable to detect a base change mutation at a single position in gene. The techniques herein would provide a set of four probes that are complementary to a short region around the single position. The first probe would be exactly complementary to the wild-type (normal) sequence for that region of the gene. The other three probes would be identical to the first, except they would substitute the three bases that are not complementary to the wild-type sequence at the position being interrogated (i.e., the interrogation position).

In this way regardless of the base change mutation, one of the probes will be perfectly complementary to the target oligonucleotide sequence. To detect any such mutation in the gene, i.e., to resequence the gene, one may define similar sets of probes for each position in the gene. For example, to resequence the 1040 bases of HIV necessary to detect drug resistance related mutations, 4160 probes are generally required. Such techniques are described in greater detail in PCT WO95/11995 which is incorporated herein by reference for all purposes. Of course, arrays such as peptide arrays will provide for different techniques of probe selection.

Once a set of probes is chosen, the layout of the probes on the chip is determined. The layout is used to design the photolithographic masks used in chip synthesis process. These designs in general are produced in electronic form and are used to fabricate the masks in a mask fabrication shop such as those widely used in the semiconductor industry.

Figure 1:
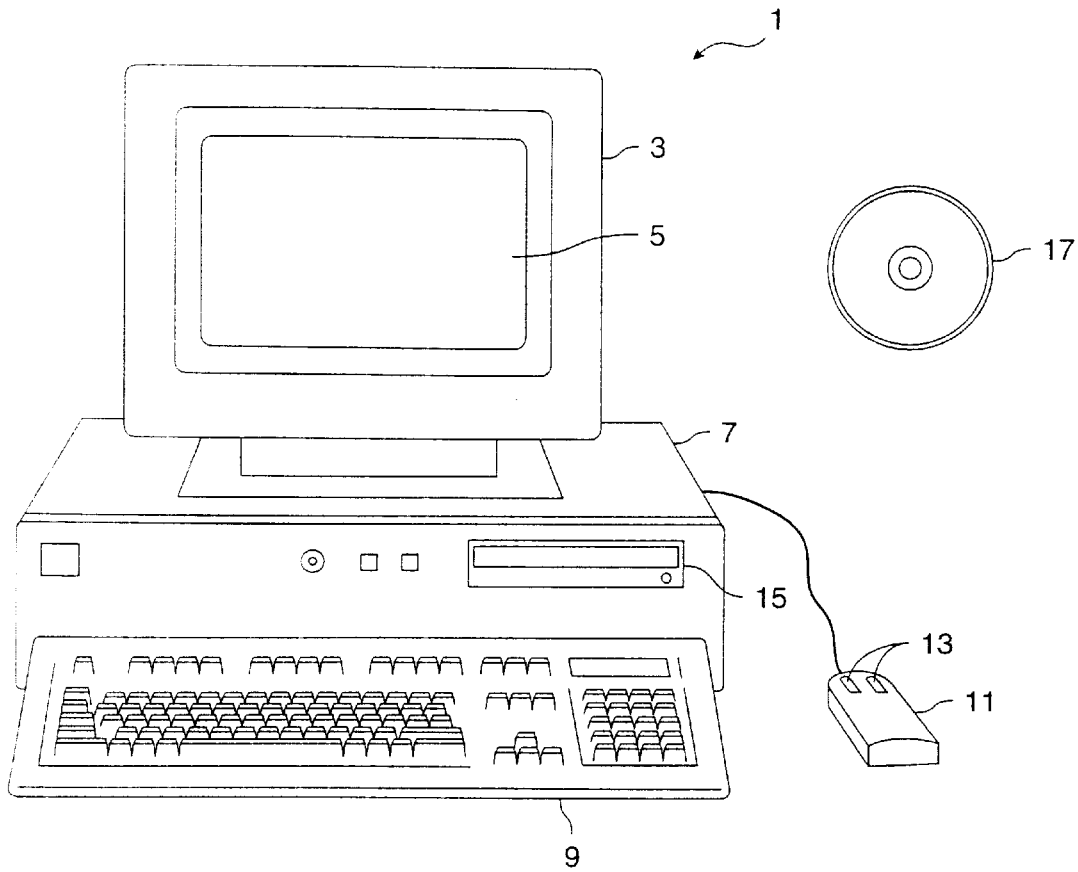
FIG. 1 illustrates an example of a computer system used to execute software embodiments of the present invention.

FIG. 1 illustrates an example of a computer system used to execute software embodiments of the present invention to generate masks for chip synthesis. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
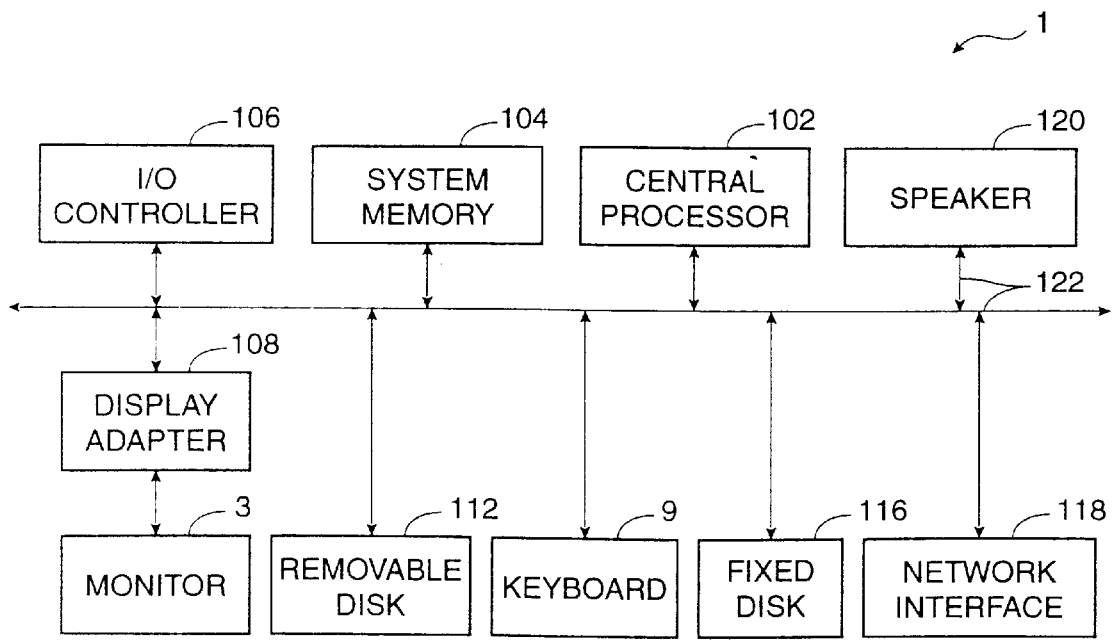
FIG. 2 shows a system block diagram of a typical computer system used to execute software embodiments of the present invention.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 102, system memory 104, I/O controller 106, display adapter 108, removable disk 112, fixed disk 116, network interface 118, and speaker 120. Removable disk 112 is representative of removable computer readable media like floppies, tape, CD-ROM, removable hard drive, flash memory, and the like. Fixed disk 116 is representative of an internal hard drive or the like. Other computer systems suitable for use with the present invention may include additional or fewer subsystems. For example, another computer system could include more than one processor 102 (i.e., a multi-processor system) or memory cache.

Arrows such as 122 represent the system bus architecture of computer system 1. However, these arrows are illustrative of any interconnection scheme serving to link the subsystems. For example, display adapter 108 may be connected to central processor 102 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. For example, software embodiments of the invention may be implemented on an IBM compatible computer, workstations from Sun Microsystems, and the like.

Light-directed chemical synthesis combines semiconductor-based photolithography and solid phase chemical synthesis. To begin the process, linkers modified with photochemically removable protecting groups are attached to a solid substrate or chip surface. Light is directed through a photolithographic mask or reticle to specific areas of the synthesis surface, activating those areas for chemical coupling. The first of a series of chemical building blocks (A, C, G, U or T) is incubated with the chip, and chemical coupling occurs at those sites which have been illuminated in the preceding step. Next, light is directed to a different region of the substrate through a new mask, and the chemical cycle is repeated.

The patterns of light and the order of chemical reagents dictate the identity of each oligonucleotide probe on the chip surface. Using combinatorial synthesis methods, millions of chemical compounds can be created rapidly in very few process steps.

Oligonucleotide probe arrays contain thousands or millions of oligonucleotide probes that can be used to recognize longer target oligonucleotide sequences (for example, from patient samples). The recognition of sample oligonucleotide by the set of oligonucleotide probes on the chip takes place through the mechanism of oligonucleotide hybridization. Oligonucleotide hybridization is the simple process in which two complementary strands of oligonucleotide join together (A pairs with T and G pairs with C). When an oligonucleotide target hybridizes with an array of oligonucleotide probes, the target will bind to those probes that are complementary to a part of the target oligonucleotide sequence.

Information about the sequence of the target oligonucleotide may be determined according to which probes hybridized with the target. Such arrays have applications for oligonucleotide probe arrays in oligonucleotide sequence analysis, oligonucleotide sequence checking, mutational analysis, mRNA expression monitoring, and medical diagnostic research.

The invention herein provides a technique for synthesizing probe arrays in which the cost of mask manufacturing is reduced. In preferred embodiments of the invention, mask costs are reduced by designing one or a few shift reticles that may be used to synthesize arrays of probes on a substrate. Accordingly, the shift reticle(s) may be used to synthesize "custom" arrays of probes, but the cost of making the mask set for such custom probes is greatly reduced on a per chip basis.

Figures 3A, 3B, 4:
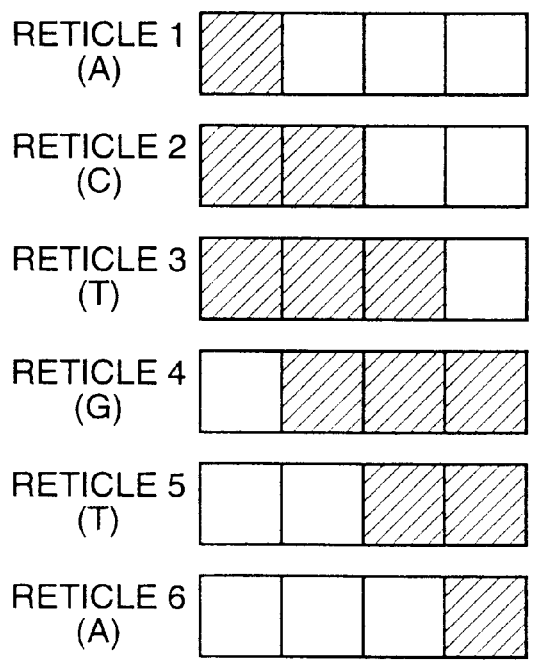
FIG. 3A illustrates a probe set that may be utilized to detect a target sequence and FIG. 3B shows a layout of the probe set on a substrate in one embodiment.
FIG. 4 shows prior art reticles that produce the probe set of FIG. 3A.

FIG. 3A illustrates a probe set that would be desirable for the evaluation of nucleic acid samples expected to contain the sequence TGACAT. To evaluate a sample to determine if its sequence is, in fact, TGACAT a set of 3-mer probes as shown in FIG. 3A may be synthesized on a substrate. If a particular sample did have the sequence TGACAT (the "target" sequence), it would be expected to hybridize to each of the probes ACT, CTG, TGT, and GTA as they are complementary. If, however, there was a variation in the second base position ("G"), lower hybridization would likely be observed in the ACT probe region as there is a single base mismatch to the target. Suppose, for example, a particular sample had the sequence TAACAT. Hybridization would not likely be observed in the ACT probe region since ACT is not perfectly complementary to the sequence TAACAT at any position.

As disclosed in PCT WO95/11995, additional probes may be synthesized to determine which variation is present at a particular position. For example, in addition to the ACT probe, the probes AAT, ATT, and AGT may be synthesized on the substrate (the interrogation position is underlined). The strong hybridization of the probe ATT, for example, would indicate that the sample is likely to be TAACAT.

FIG. 3B illustrates probe sets that would be desirable for determining mutations in samples expected to contain the sequence TGACAT. Each column contains a set of four probes for determining a nucleotide in the sample corresponding to the interrogation position. As shown, each of the four probes in a column differ at the interrogation position. In a preferred embodiment, probes with the same nucleotide at their respective interrogation position are placed in a row, thereby forming an A-lane, C-lane, T-lane, and G-lane. The wild-type probes from FIG. 3A are designated with a "*" within the probe region. Typically, there are many multiples (e.g., hundreds or thousands) of identical probes within a probe region or cell.

FIG. 4 shows prior art reticles that would be utilized to synthesize the ACT, CTG, TGT, and GTA probes of FIG. 3A. Reticles 1 and 6 are for adding the nucleotide A onto the substrate. Reticle 2 is for adding nucleotide C onto the substrate. Reticle 4 is for adding nucleotide G onto the substrate. Lastly, reticles 3 and 5 are for adding the nucleotide T onto the substrate. Utilizing these reticles, the synthesis can be viewed as repetitive additions of A, C, T, and then G, with unnecessary addition steps skipped.

In the figures depicting reticles, shaded portions represent openings through the reticle through which light will deprotect areas on the substrate. Monomers (e.g., nucleotides) will then be washed over the substrate so that the monomers may bind in the deprotected regions. Although in preferred embodiments, the monomer addition regions of the reticles are openings, the monomer addition regions may be closed on the reticles in a similar matter.

Figure 5:
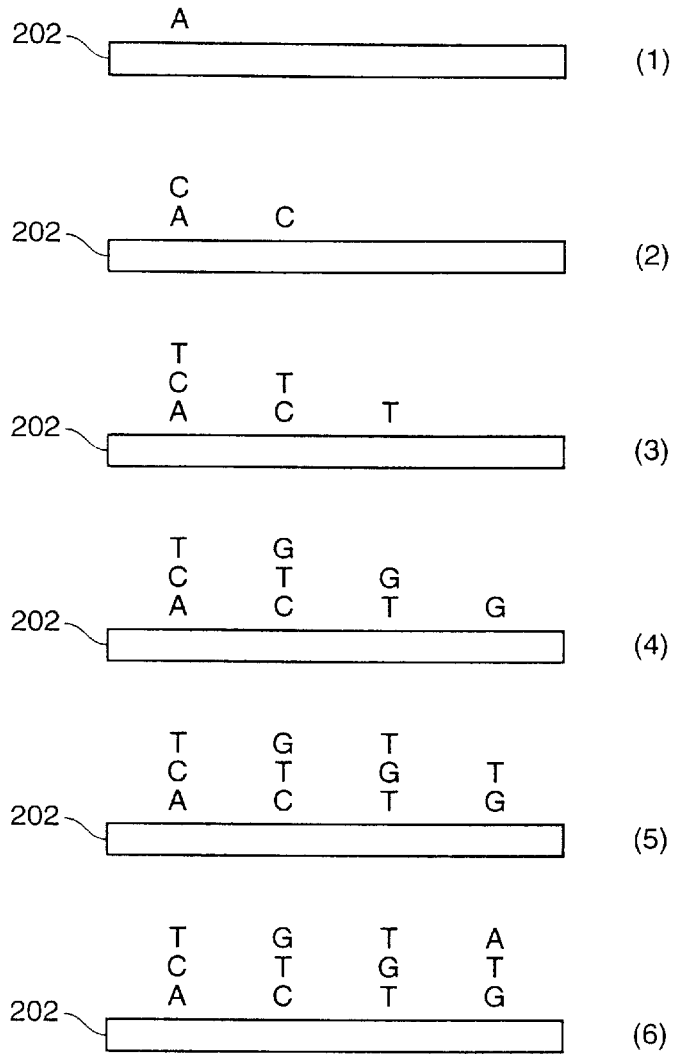
FIG. 5 shows the prior art addition of monomers to produce the probe set of FIG. 3A.

FIG. 5 shows the prior art addition of nucleotide monomers to produce the probe set. Reticles 1–6 are utilized to sequentially add monomers to a substrate 202. At the top of FIG. 5, reticle 1 is utilized to add the nucleotide A to the substrate at a location specified by the monomer addition region of the reticle. Then, reticle 2 is utilized to add the nucleotide C to the substrate as specified by the reticle. The process continues through reticle 6 which results in four probes that may be utilized to analyze the target sequence.

Although the process in FIG. 5 can be viewed as repetitive additions of A, C, T, and G, in some instances, a particular monomer addition step may be "skipped." For example, in FIG. 5, the additions of A and C after the G addition are skipped in the second cycle of A, C, T, G additions. Thus, six reticles are needed for the synthesis of these probes. In the worst case, an addition of A, C, T, and G would be needed for each of the n monomers in the probes. Accordingly, in the worst case, n*4 reticles would be needed to synthesize a probe set. In many cases, this number is reduced to some number m where the sequence allows, as in the above example, where m would be 6 which is better than the worst case of 12 (3*4) reticles. As the number of monomers in the probes grows, however, the number of required reticles can become quite large thereby increasing costs.

The present invention provides techniques for synthesizing probe arrays using far fewer reticles, which greatly reduces costs. With one embodiment of the invention, as few as one reticle may be used to make, for example, the exact complement probe set. An additional reticle may be utilized to make probes with nucleotide variations at an interrogation position and other reticles may be utilized to fabricate different probe sets on the substrate (e.g., probe sets with different probe lengths).

Set of Shift Reticles

In one embodiment, the present invention utilizes a set of shift reticles to synthesize desired probes on a substrate. The set of shift reticles includes a single reticle for each monomer that is to be added to the substrate. Utilizing these reticles, the length and interrogation position of the probes may be specified at synthesis time, e.g., after the reticles have been generated.

Figure 6:
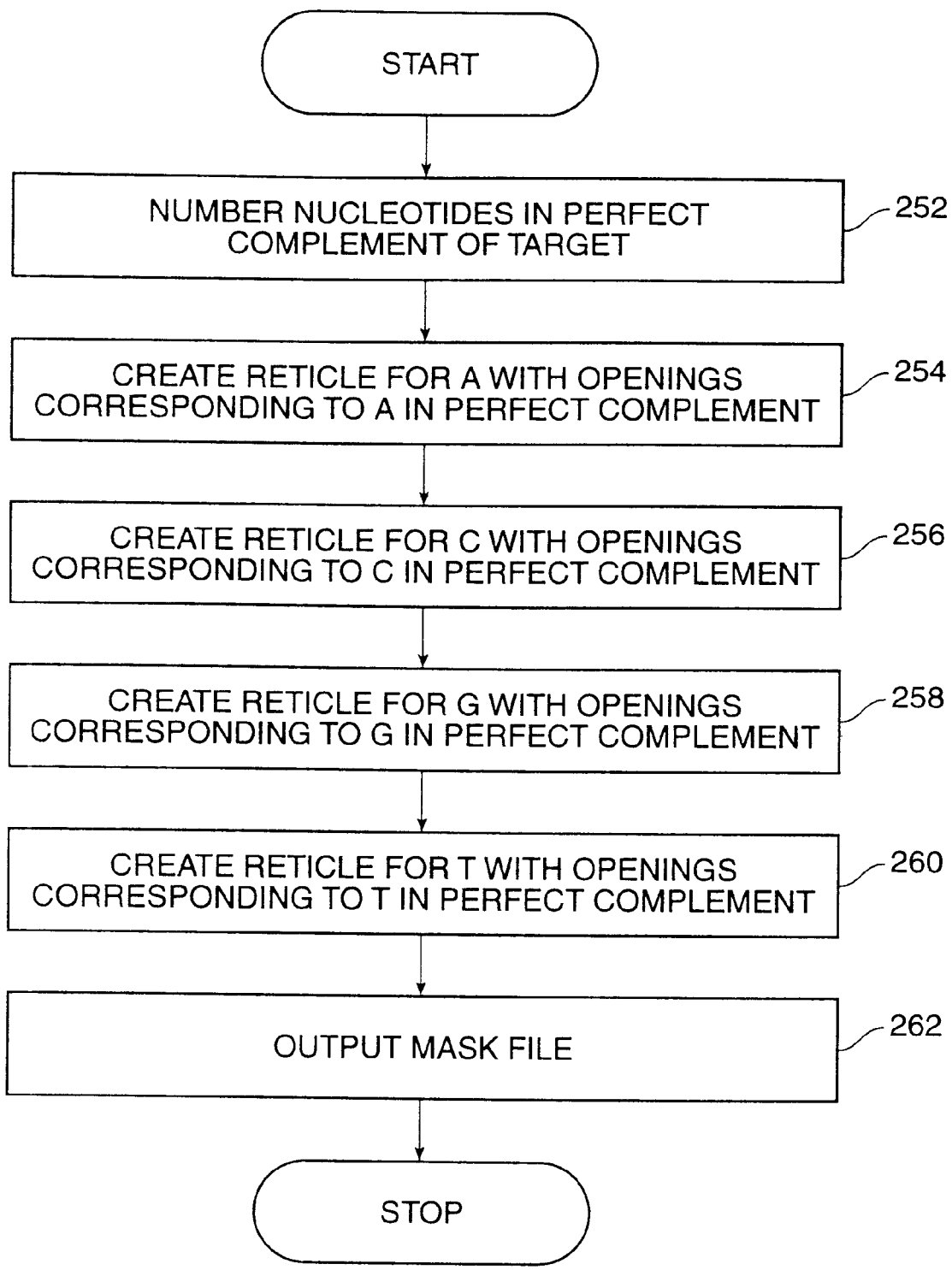
FIG. 6 shows a high level flow of a process of generating reticles according to one embodiment of the present invention.

FIG. 6 shows a high level flow of a process of generating a shift reticle set. At step 252, the nucleotides in the perfect complement of the target sequence are numbered. Thus, for the target sequence shown in FIG. 3A, the nucleotides may be numbered 1–6. Four 1×6 reticles will subsequently be formed for synthesizing probes to detect the target sequence. Each of the four reticles will be utilized to add a different monomer (e.g., A, C, G, T) onto the substrate.

Figure 7:
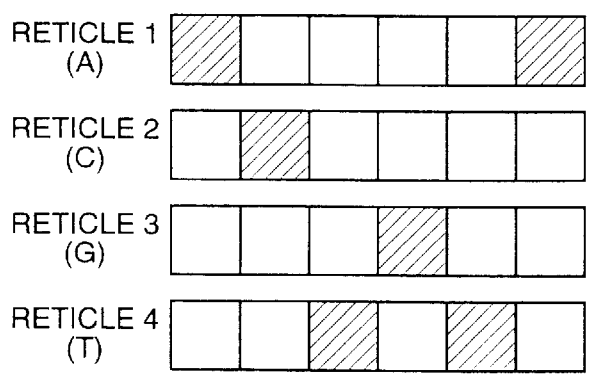
FIG. 7 shows shift reticles that produce the probe set of FIG. 3A.

At step 254, a reticle for adding the nucleotide A to the substrate is created. The reticle is designed with openings corresponding to each A in the perfect complement to the target sequence. Thus, for the perfect complement ACTGTA, the reticle would have openings corresponding to nucleotides 1 and 6. Reticle 1 of FIG. 7 shows a reticle produced in this manner.

At step 256, a reticle for adding the nucleotide C is created in a similar manner. The reticle is designed with openings corresponding to each C in the perfect complement to the target sequence. Therefore, the reticle is designed with an opening corresponding to nucleotide 2 in the target. Reticle 2 of FIG. 7 shows a reticle for adding nucleotide C. Steps 258 and 260 create reticles 3 and 4 shown in FIG. 7 in a similar manner for nucleotides G and T, respectively.

At step 262, a computer file containing the design of the masks is output. This file may be utilized by a mask generating system to produce the masks used in synthesis. A system for designing masks is described in U.S. Pat. No. 5,571,639, which is hereby incorporated by reference for all purposes.

Figure 8A:
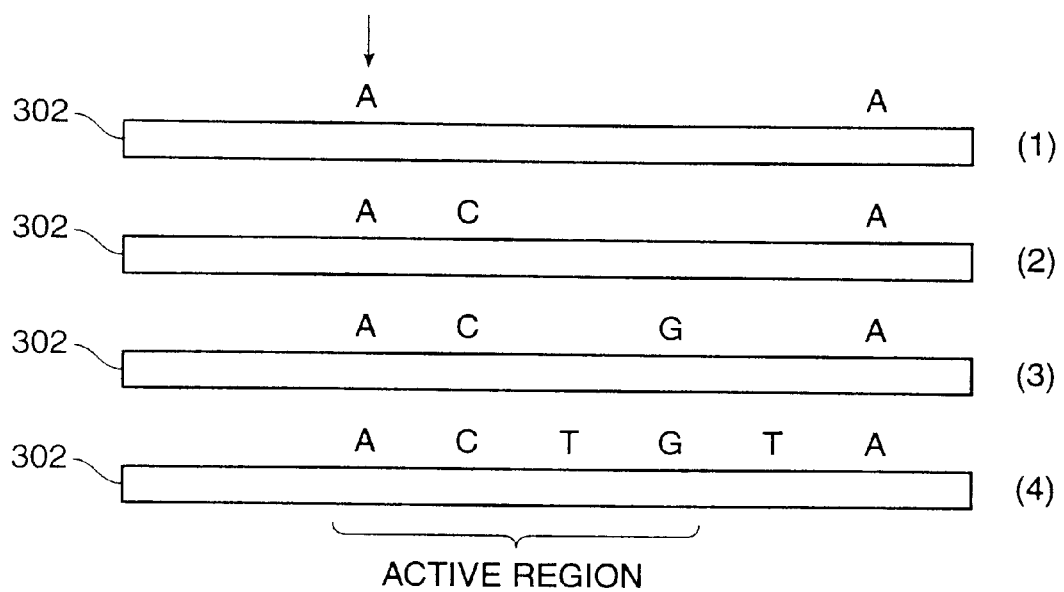
FIGS. 8A–8C shows the addition of monomers using the shift reticles to produce the probe set.
Figure 8B:
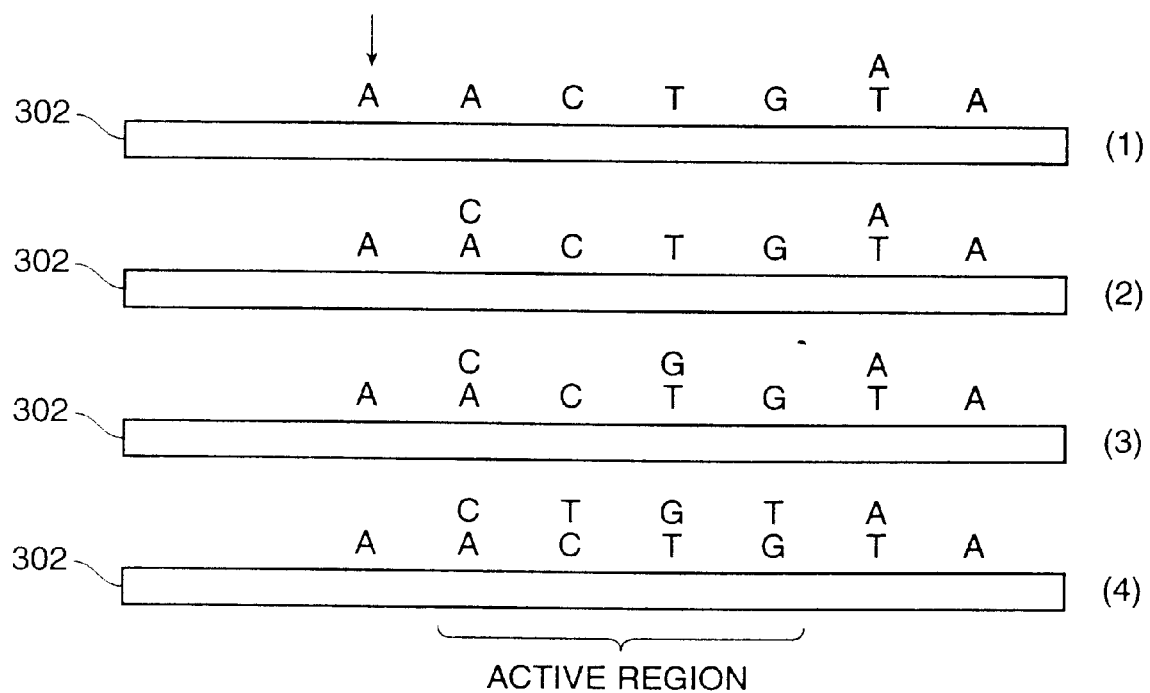
Figure 8C:
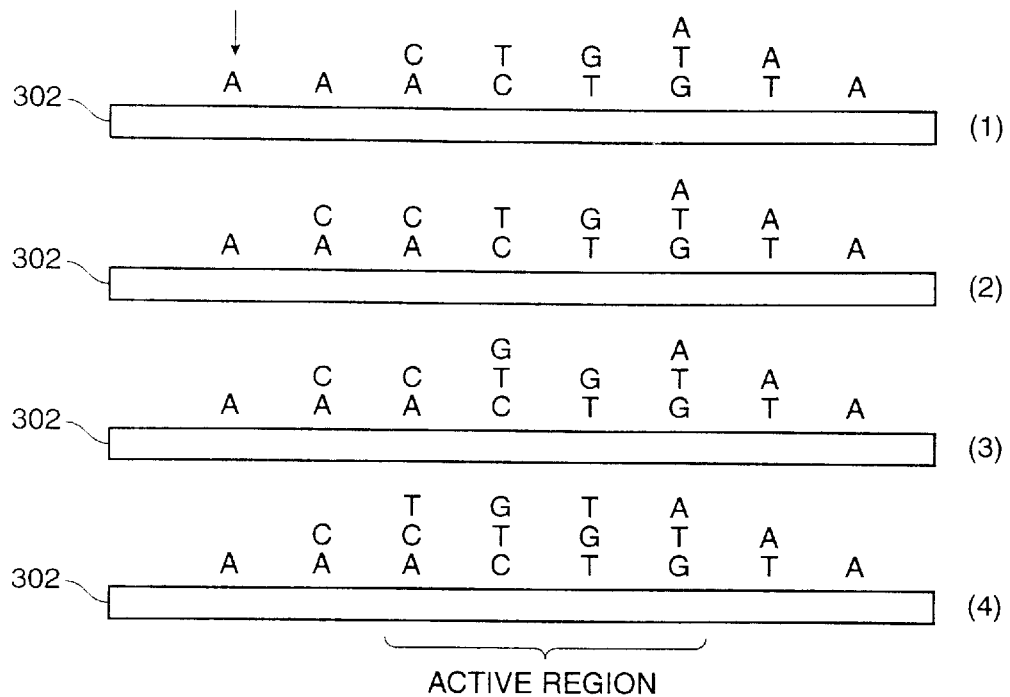

FIGS. 8A–8C show the addition of monomers using the shift reticles to produce the probe set. In FIG. 8A, the shift reticles are used to produce a single "layer" of monomers on a substrate 302. By a "layer" of monomers, it is meant that each synthesis cycle of monomer addition steps uniformly adds monomers to specified locations on the substrate. As shown in FIG. 8A, the specified locations may include the entire active region of the substrate. However, as will be shown in FIG. 18, the specified locations may include only a subset of locations of the active region.

Referring still to FIG. 8A, reticle 1 is initially used to add the nucleotide A onto the substrate. Reticle 2 is subsequently utilized to add the nucleotide C to the substrate, which is followed by the addition of nucleotides G and T utilizing reticles 3 and 4, respectively. With one synthesis cycle of A, C, G, and then T, a single layer of monomers has been added to the active region of the substrate which is shown as the four centermost positions on the substrate. The number in parenthesis indicates the reticle being used. The arrow indicates where the reticles are aligned with the substrate (i.e., the first possible opening in each reticle). The reticles will all be shifted one position after each synthesis cycle.

In FIG. 8B, the reticles are shifted one position to the left relative to the substrate as indicated by the arrow in the figure (compare to FIG. 8A). Each reticle is then cycled through to add each of the different monomers onto the substrate at locations specified by the reticles. Again, the reticles add a single layer of monomers to the active region of the substrate. Although the reticles are shown shifted or translated to the left, the reticles may, of course, be shifted to the right or any other direction.

In FIG. 8C, the reticles are again left shifted by one position as indicated by the arrow in the figure. The reticles are cycled through adding nucleotides A, C, G, and T to the substrate as specified by the openings in the reticles. After the last reticle is utilized, four probes that are perfectly complementary to the target sequence have been synthesized at the centermost positions of the substrate as shown at the bottom of FIG. 8C. These four probes represent the active region of the substrate. The probes shown that are not in the active region of the substrate will be called the "edge" of the substrate. These edge probes are typically ignored during analysis or sequencing of a sample.

For simplicity, the monomer addition regions of a reticle have been shown to add a single monomer onto the subject substrate. In practice, each monomer addition region of a reticle adds hundreds or thousands of monomers to the area specified by the opening. Similarly, the reticles typically synthesize hundreds of rows of probes on the substrate. In a preferred embodiment, the probes are synthesized in multiples of four rows where the probes in each row differ from the other by a single nucleotide at an interrogation position.

Figure 9A:
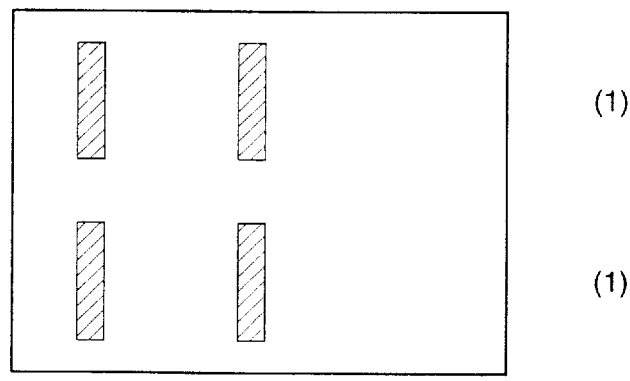
FIGS. 9A–9B show reticles for producing multiple probe sets.
Figure 9B:
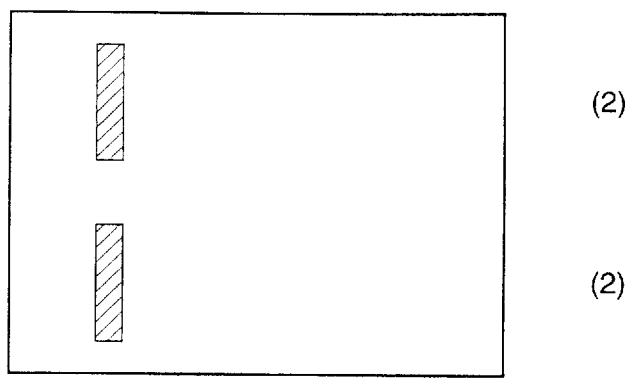

FIGS. 9A–9B show reticles that may be used to produce multiple probe sets for the target sequence shown in FIG. 3. FIG. 9A shows a reticle similar to reticle 1 in FIG. 7. However, this reticle would be utilized to produce two sets of four rows of probes. Likewise, FIG. 9B shows a reticle similar to reticle 2 in FIG. 7 that would be utilized to produce two sets of four rows of probes. The reticles for nucleotides G and T are not shown but would be similarly produced.

Each of these four shift reticles would be utilized to produce two sets of four rows of probes on the substrate that would be complementary to the target sequence. Each synthesis cycle in the synthesis produces a set of n-mer complementary probes to this target. Thus, after three cycles through the shift reticles, the substrate contains a set of 3-mer complementary probes. The length of complementary probes may be selected at synthesis time by the number of synthesis cycles of monomer addition steps that are used, where a "synthesis cycle" is defined as cycling through each of the monomers to be added to the substrate. One synthesis cycle results in adding a layer of monomers to specified locations on the substrate, typically the active region of the substrate.

Figure 10:
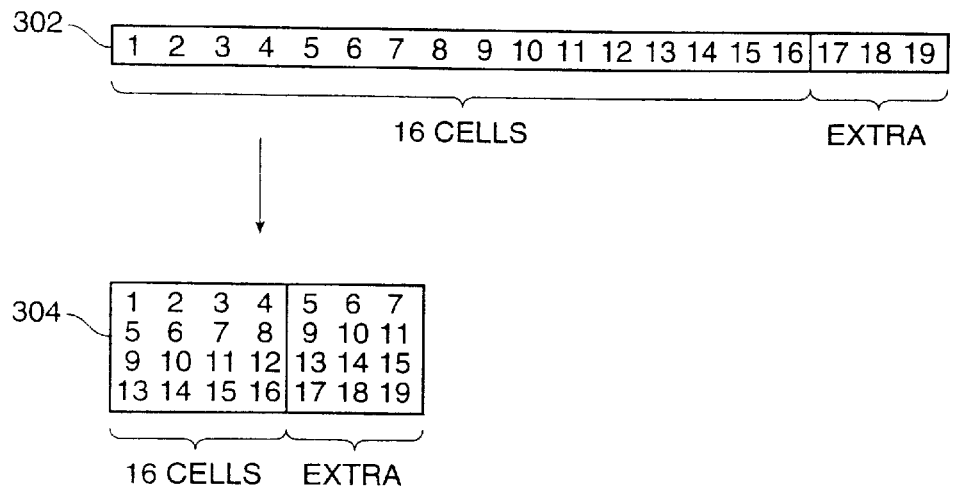
FIG. 10 shows the transformation of a linear reticle into a rectangular reticle.

FIG. 10 shows the transformation of a linear reticle into a rectangular reticle. Although the shift reticles have been shown as long linear reticles, the linear reticles may be transformed into a rectangular shift reticle. A linear reticle 302 includes sixteen active cells and three extra cells. The extra cells are the cells added to the reticle for shifting relative to the substrate. Typically the number of cells in the linear shift reticle will be substantially greater but the simple reticle is shown for illustration purposes.

When transforming the linear reticle into a rectangular reticle, the sixteen active cells are placed in a rectangular region with the appropriate extra cells at the edge. Thus, a rectangular reticle 304 was formed by placing cells 1–16 into a square region of the reticle. Each row of the rectangular reticle ended with the same number of extra cells as was in the linear reticle, these extra cells continuing sequentially after the active cells. The resulting rectangular reticle is a shift reticle that forms rows of probes for a target sequence.

Figure 11A:
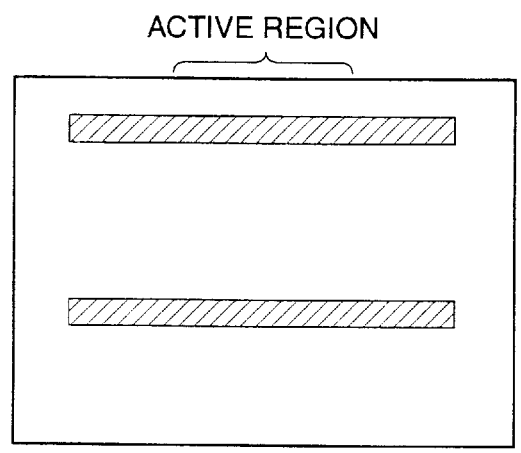
FIG. 11A shows a reticle for adding monomers at an interrogation position.
Figure 12A:
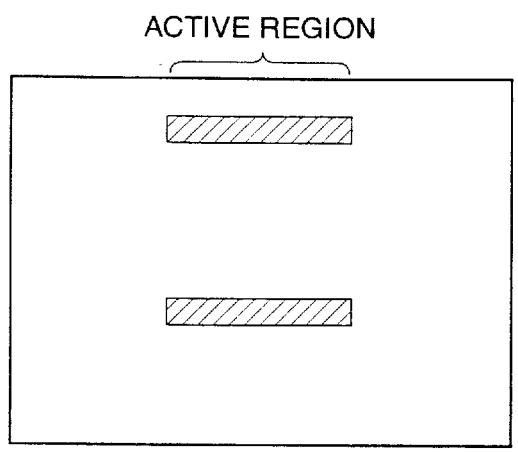
FIG. 12A shows another reticle for adding monomers at an interrogation position.

In order to add differing monomers at an interrogation position, reticles such as those shown in FIGS. 11A and 12A are utilized. FIG. 11A shows a reticle that is used to couple interrogation position monomers on the substrate. The reticle includes multiple rows of openings that are utilized to add a monomer to the probes. These rows are perpendicular to the reticles shown in FIGS. 9A and 9B.

The reticle in FIG. 11A is first utilized to add a monomer like nucleotide A to a row of probes (i.e., the A-lane). The reticle is then shifted downwards to the next row of probes and a different monomer like nucleotide C is then added to this row of probes (i.e., the C-lane). This process is continued until a different monomer is added to the interrogation position for each row in a set of probes. For a deletion, a monomer is not added to a row of probes.

Thus, in order to produce 5-mer probes with an interrogation position at the third position in the probes, one performs two synthesis cycles of monomer addition steps with the shift reticles to produce 2-mer probes in the active region of the substrate. Then the interrogation position reticle is utilized to add a different monomer to each row of probes by shifting the mask in a direction perpendicular to the direction that the shift reticles are shifted. Except in the case of deletions, the interrogation position reticle also adds a layer of monomers in the active region of the substrate with one synthesis cycle. Then, after shifting the shift reticles two positions (the extra position accounts for the synthesis cycle utilized by the interrogation position reticle), the shift reticles are utilized to add the last two monomers to the probes by performing two synthesis cycles of monomer addition steps.

Figure 11B:
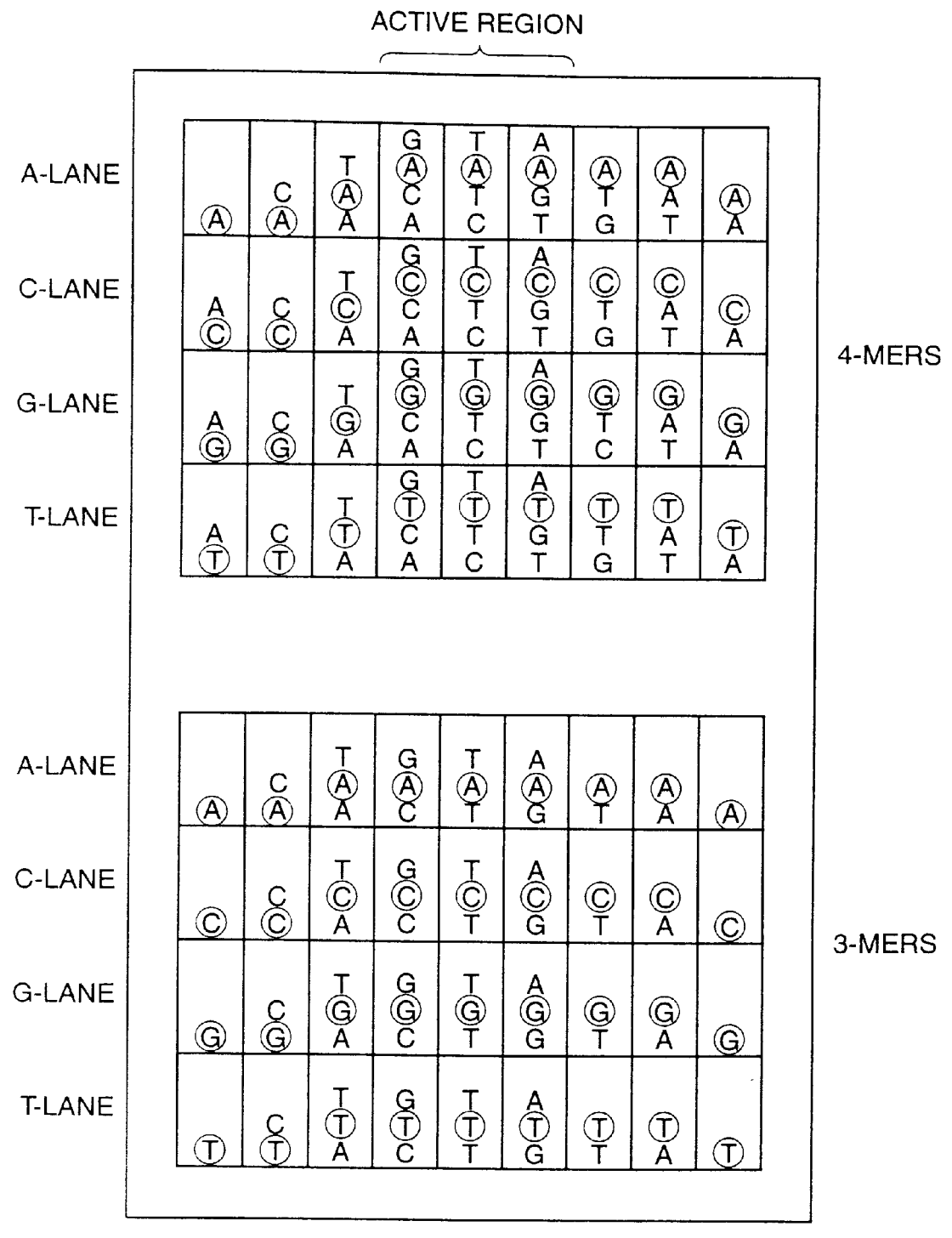

FIG. 11B shows probes on a chip that vary at an interrogation position. The top half of the chip includes 4-mer probes with the interrogation position at the third nucleotide in the probe (the interrogation nucleotide is circled for easy identification). As shown, there are 4-mer probes in the active region of this half of the chip. The bottom half of the chip includes 3-mer probes in the active region that were synthesized using the same shift reticles and the interrogation position reticle at the same time with the use of one additional reticle which allows different length probes to be synthesized on the chip at the same time. This reticle will be described in more detail in reference to FIG. 13A.

The shift reticles of the present invention are target structure specific but not sequence specific. For example, the shift reticles may be utilized to synthesize probes complementary to the sense or anti-sense strands of DNA. Additionally, shift reticles that produce probes complementary to TGACAT may also be used to produce probes complementary to AGTCTA by switching the A and T nucleotides utilized with the shift reticles. Accordingly, at synthesis time, one may specify characteristics of the probes by selecting the order of shift reticles in a synthesis cycle, the monomers in a synthesis cycle, the monomers associated with each of the shift reticles, and the interrogation position.

Figure 11C:
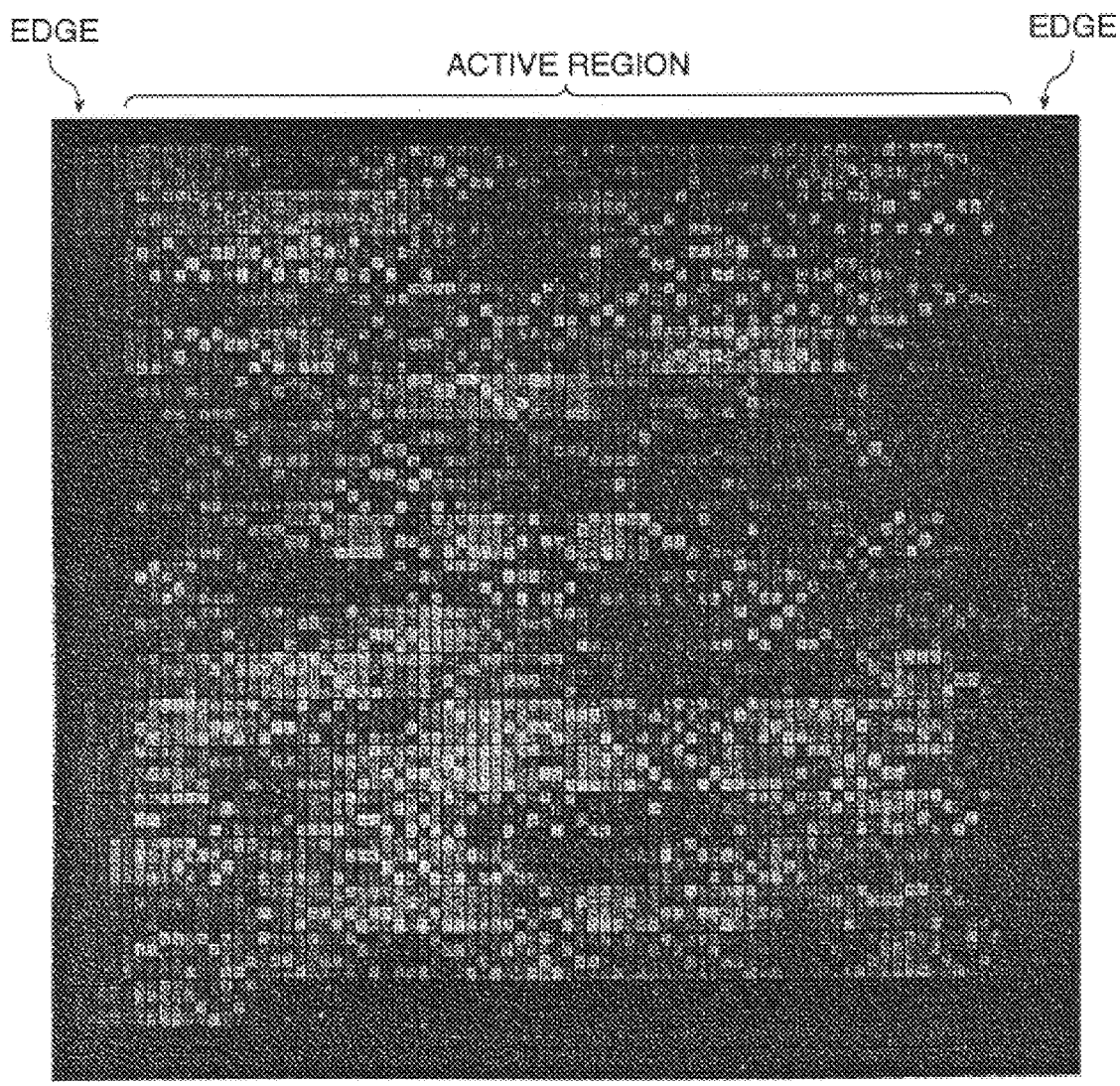
FIG. 11C is an image of a chip produced with a reticle similar to the one in FIG. 11A.

FIG. 11C is an image of a chip that was produced in the manner described above. The chip has 20-mer probes with an interrogation position at a central position. The chip is for sequencing a 1000 base-pair sequence of HIV. It should be understood that the examples described above are simplified to aid the readers understanding of the invention. The chip images show actual chips and are therefore more complex, but they nevertheless utilize the principles of the present invention extended to a larger scale.

The probes in the edge regions of the substrate will still bind to the labeled target with varying hybridization intensities as shown on the right side of the chip in FIG. 11C. However, it is difficult for one to visually identify where the active region of the chip begins or ends. In a preferred embodiment, an interrogation position reticle as shown in FIG. 12A is utilized. This reticle has openings that only correspond to or overly the active region of the substrate. Because the openings will not be above the edge regions of the substrate, the probes at the edge regions of the substrate will not receive the interrogation position nucleotides. In this manner, the probes in each column in the edge regions will be identical and therefore, the edge region will appear as stripes in the image of the chip so the start of the active region may be more easily identified. This is shown on the left side of the chip in FIG. 11C.

Figure 12B:
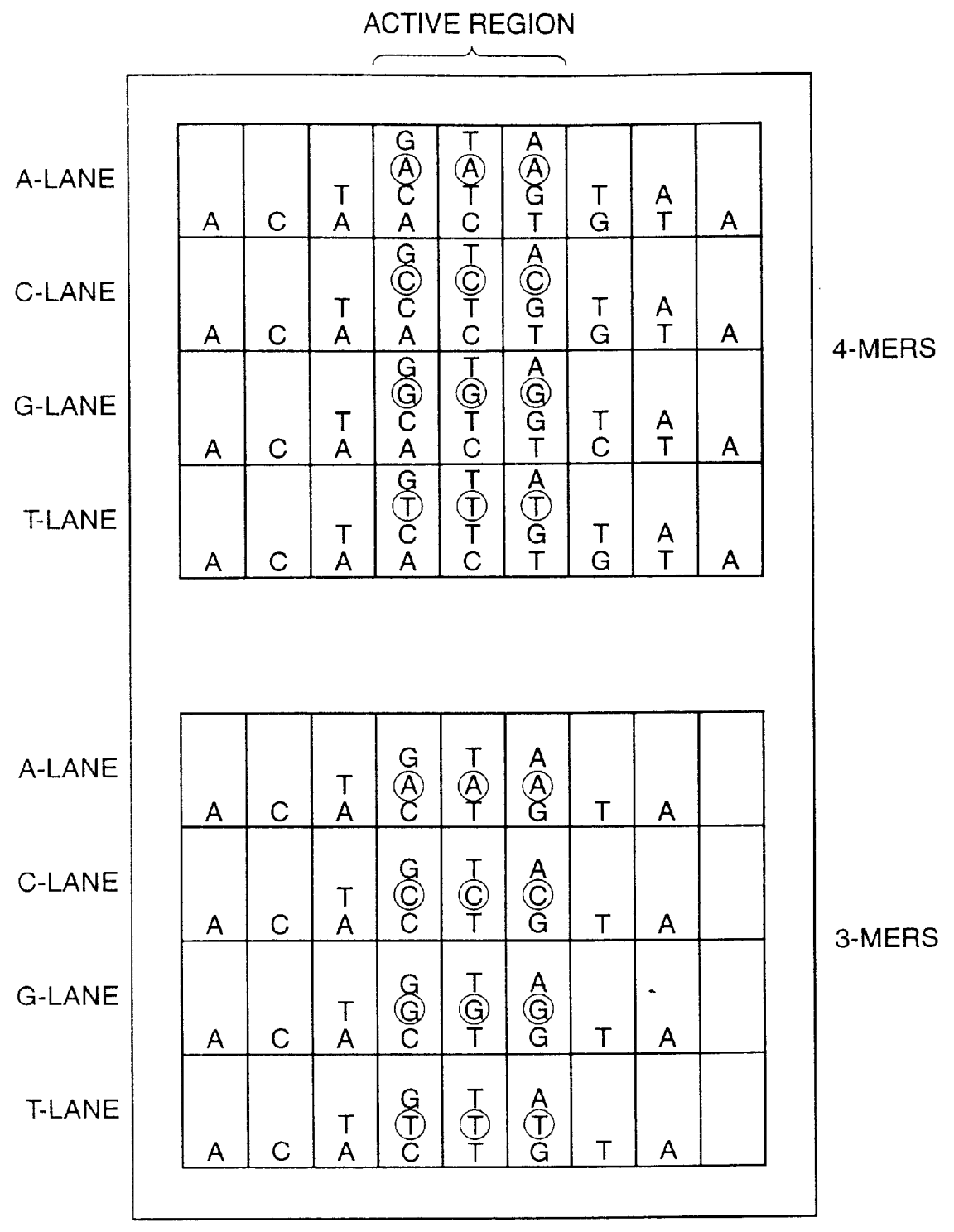

FIG. 12B shows probes on a chip that vary at an interrogation position but were synthesized utilizing the reticle shown in FIG. 12A. The top half of the chip includes 4-mer probes with the interrogation position at the third nucleotide in the probe. As shown, there are 4-mer probes in the active region lane of this half of the chip. The circled interrogation nucleotides were only added in the active region. Thus, the probes in each column outside the active region (edges) are identical. As they are identical, the resulting stripes may be utilized to identify the edges of the chip after hybridization and scanning. The bottom half of the chip includes 3-mer probes that were synthesized using the reticle shown in FIG. 13A.

Figure 12C:
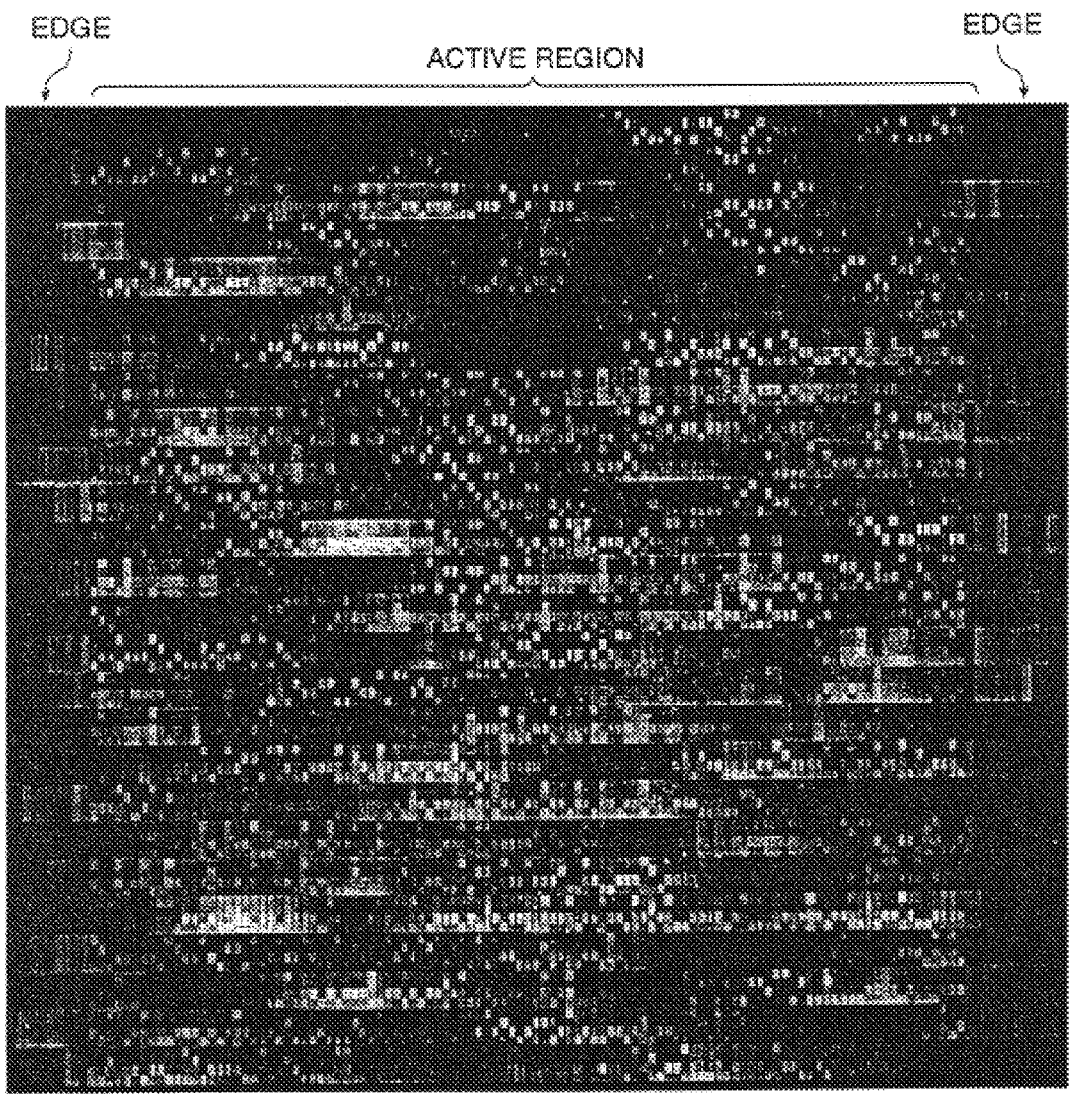
FIG. 12C is an image of a chip produced with a reticle similar to the one in FIG. 12A.

A chip synthesized as described above is shown in FIG. 12C where the edge regions may be easily identified by the stripes. The chip has 20-mer probes with an interrogation position at a central position. The chip is for sequencing a 2,500 base-pair sequence of HIV.

Utilizing these shift reticles and the interrogation position reticle, any length probe with any substitution position may be synthesized for a target sequence limited only by the size of the reticles. Typically, the size of the reticles is equal to the size of the target along a row of the substrate plus the desired length of the synthesized probes minus one. For example, if there are 100 columns of cells on the chip and the target sequence is equal to or longer than 100 monomers, the reticles may be 111 cells (or possible monomer addition regions) wide for 12-mer probes (i.e., 100+12−1).

With the present invention, five reticles may be utilized to sequence any length probe with any interrogation position for the target sequence. Furthermore, the length of the probes and the interrogation position need not be determined before synthesis. After the reticles are produced, the specific probes that are produced on the substrate may be determined at synthesis time by indicating the number of cycles of monomer addition steps and the cycle where the interrogation position reticle will be utilized.

Figure 13A:
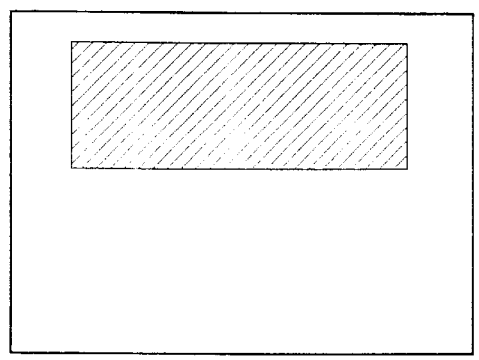
FIG. 13A shows a reticle for producing multiple probe set of different lengths and FIG. 13B shows a chip with multiple length probe sets.

A reticle as shown in FIG. 13A may be utilized to generate probes of varying length with the lengths being determined at synthesis time if desired. The reticle includes an opening which will allow light to strike a set of probes. The reticle may be utilized in conjunction with the shift reticles so that only the top half of the chip is deprotected. For example, the reticle may be utilized to add a first layer of nucleotides only to the top half of the chip. After the first layer of nucleotides has been added, synthesis may continue but now by adding nucleotides to the whole chip. It is in this manner that the 4-mer and 3-mer probes of FIGS. 11B and 12B were produced.

Figure 13B:
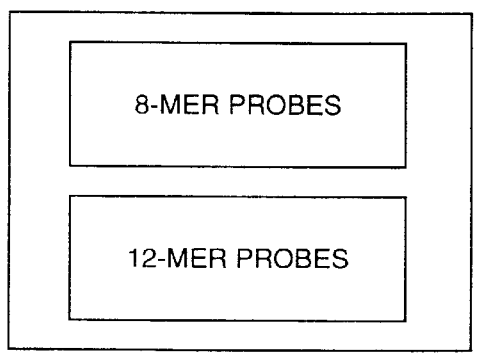

Alternatively, the reticle of FIG. 13A may be utilized to stop synthesis. After probes have been synthesized in a region, the region specified by the reticle is deprotected and a capping reagent may be added to the substrate so that subsequent exposure to light will not deprotect the probes in this region. The capping region may be DMT or any other known capping reagent. Utilizing this reticle, one region of the substrate may contain probes that are of a different length than another area of the substrate. For example, the substrate shown in FIG. 13B includes 8-mer probes and 12-mer probes. The 8-mer probes were first formed on the whole chip and then the reticle of FIG. 13A was utilized to cap the probes on the top half so that subsequent exposure to light would not result in the addition of subsequent monomers.

The region for the 12-mer probes was not capped so the subsequent addition of monomers resulted in 12-mer probes.

Additionally, the reticle shown in FIG. 13A may be utilized to synthesize probes with nucleotide deletions. For example, by utilizing the reticle to skip a cycle of nucleotide additions, probes with deletions may be synthesized.

Figure 14A:
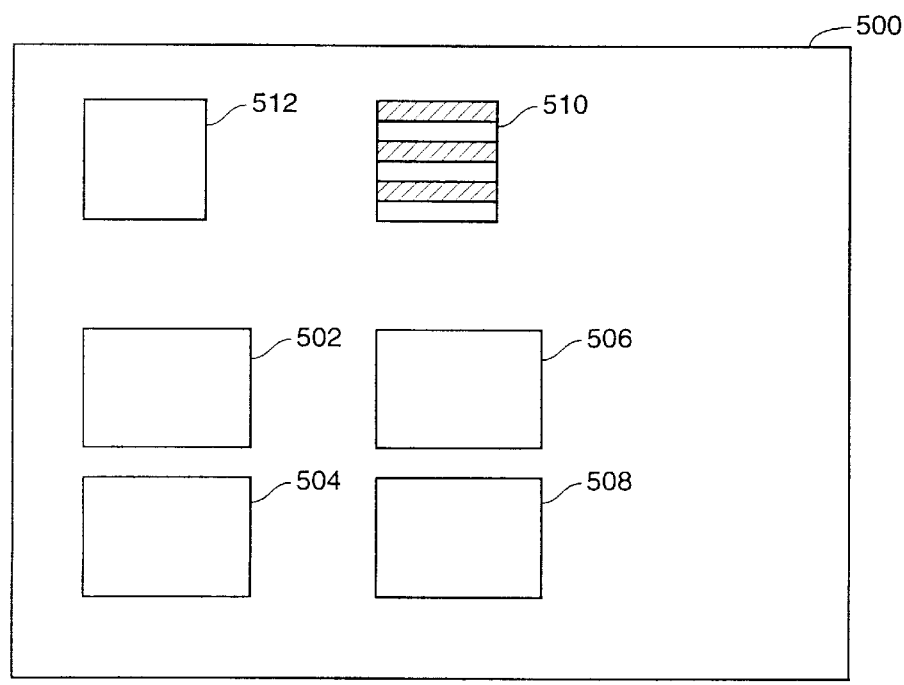
FIG. 14A is a mask including multiple reticles.

FIG. 14A is a mask including multiple reticles. A mask 500 includes shift reticles 502, 504, 506, and 508, one for each nucleotide monomer. The mask also includes an interrogation position reticle 510 which adds monomers at an interrogation position over the active region of the substrate. Additionally, the mask includes a reticle 508 which is utilized to deprotect the entire surface of the substrate in order to cap the probes after synthesis. Although FIG. 14A shows a mask that includes multiple reticles, the present invention may be advantageously utilized in those systems where each mask includes a single reticle.

Figure 14B:
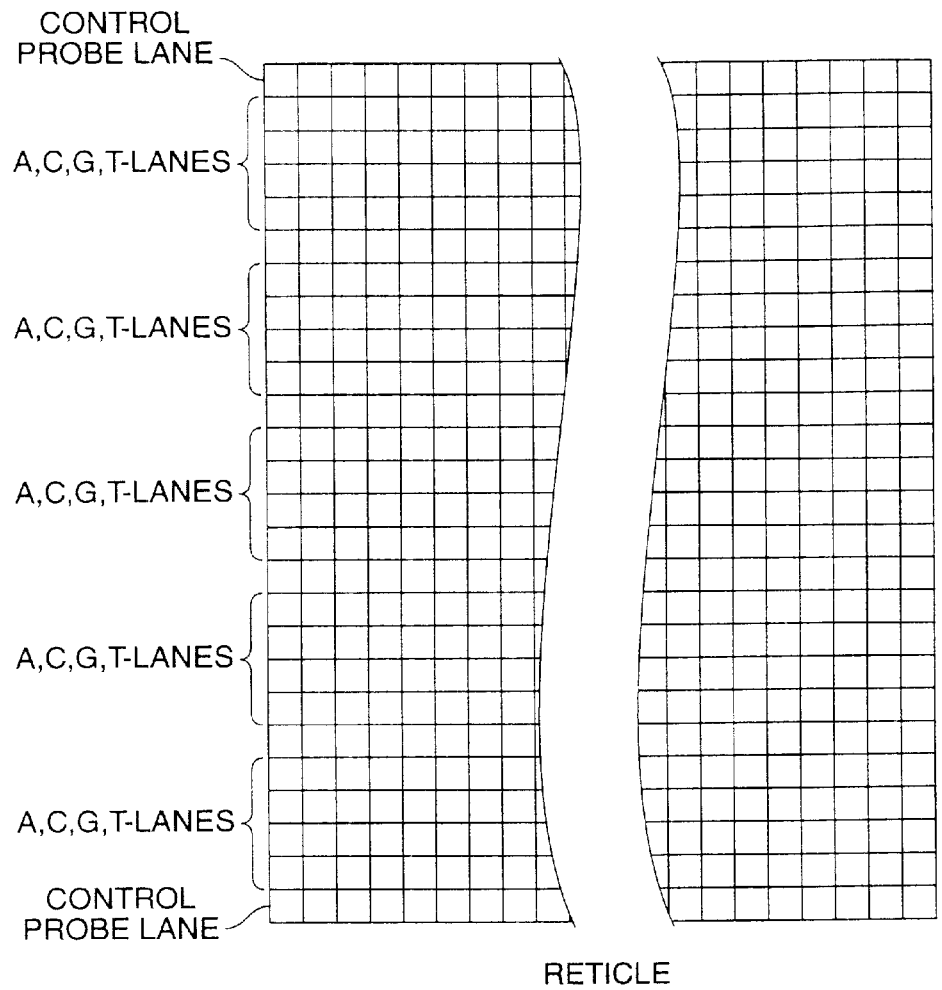
FIG. 14B shows the layout of a reticle in one embodiment.

FIG. 14B shows the layout of a reticle in one embodiment. The majority of the reticle includes rows with monomer addition regions for repeating groups of A, C, G, and T lanes of the substrate. The monomer addition regions for each group of lanes are typically the same as shown in FIGS. 9A and 9B. Each group of rows corresponding to the A, C, G, and T lanes may differ in order to synthesize probes complementary to different sections of the target. For example, one group may be for synthesizing probes for identifying nucleotides at positions 500–599 while the next group is for synthesizing probes for identifying nucleotides at positions 600–699.

The top and bottom rows of the reticle in FIG. 14B are for producing probes complementary to a control oligonucleotide sequence (i.e., control probe lanes). The control sequence is a known sequence that is added to the target to allow easier identification and/or alignment of the active region of the chip after scanning.

Figure 14E:
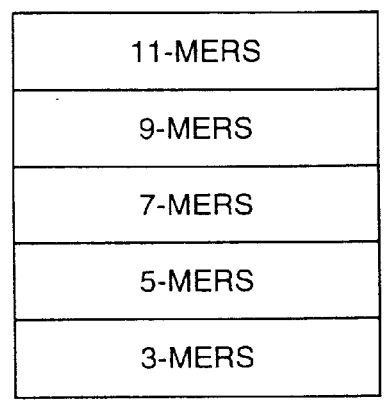
FIG. 14E shows a sample chip layout.
Figure 14C:
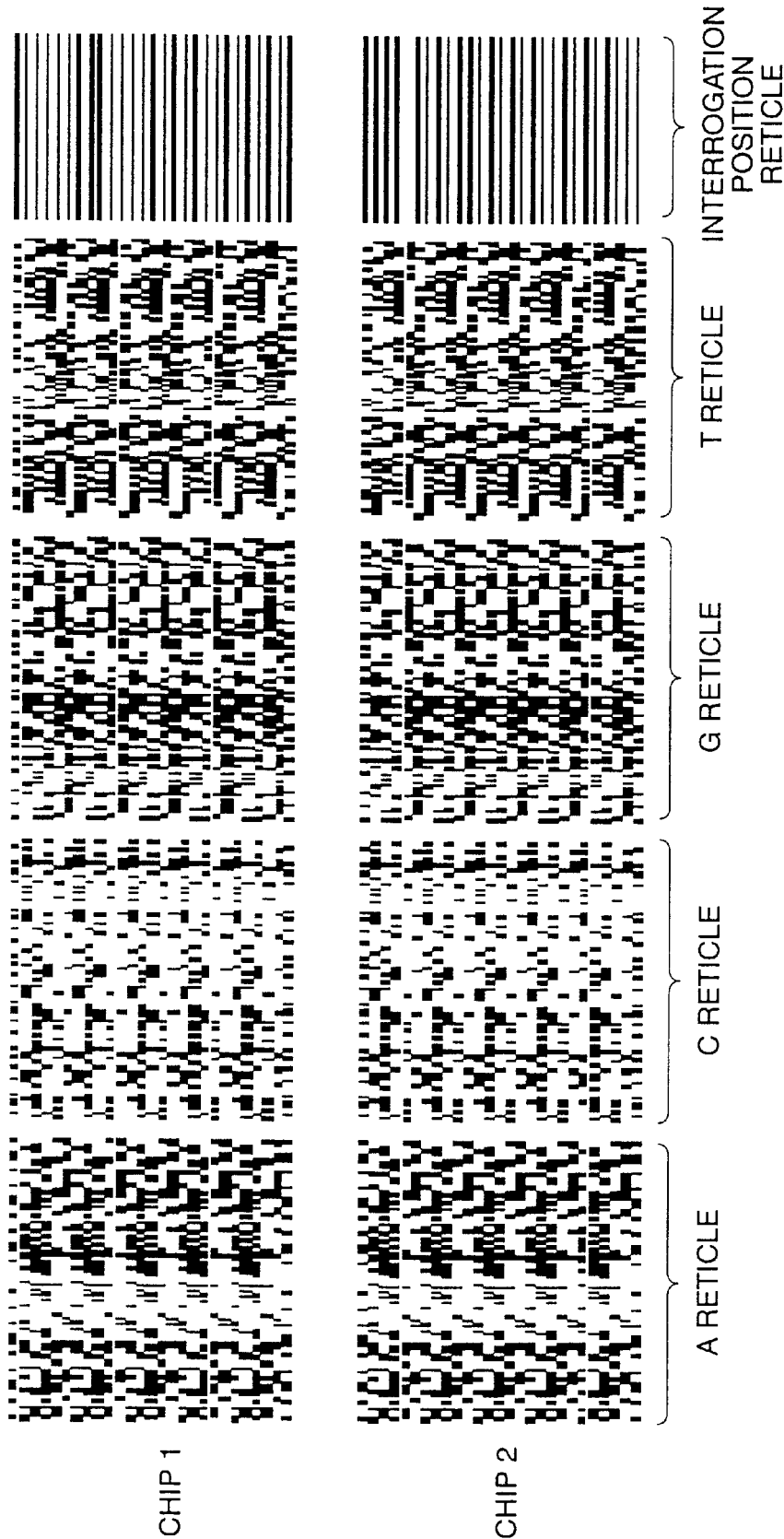
FIG. 14C shows reticles for synthesizing probes on two chips simultaneously.

FIG. 14C shows reticles for synthesizing probes on two chips simultaneously. As shown, there are identical A reticles, C reticles, G reticles, T reticles, and interrogation position reticles for each chip (denoted chip 1 and chip 2). These reticles reside on the same piece of glass so that two identical chips may be produced simultaneously. Thus, if the synthesis cycle begins with A, the two A reticles would be utilized. The glass would then be shifted so that the next nucleotide reticle is over the chips to add the next nucleotide in the synthesis cycle, and so forth. At the next synthesis cycle, the reticles would be positioned over the chip at a position shifted horizontally relative to the chip. Accordingly, the nucleotide reticles are wider than the chips.

The interrogation position reticles may be utilized to synthesize nucleotides at an interrogation position in the probes on the chips. During the synthesis cycle which is designated to add the interrogation position nucleotides, the glass is shifted vertically relative to the chip. One should understand that although the nucleotide reticles are described as being shifted horizontally and the interrogation position reticles as being shifted vertically, the reticles may be shifted any direction. Also, the reticles for chip 1 and chip 2 need not be identical, nor limited to two chips. Accordingly, multiple different chips may be synthesized with the present invention simultaneously.

Figure 14D:
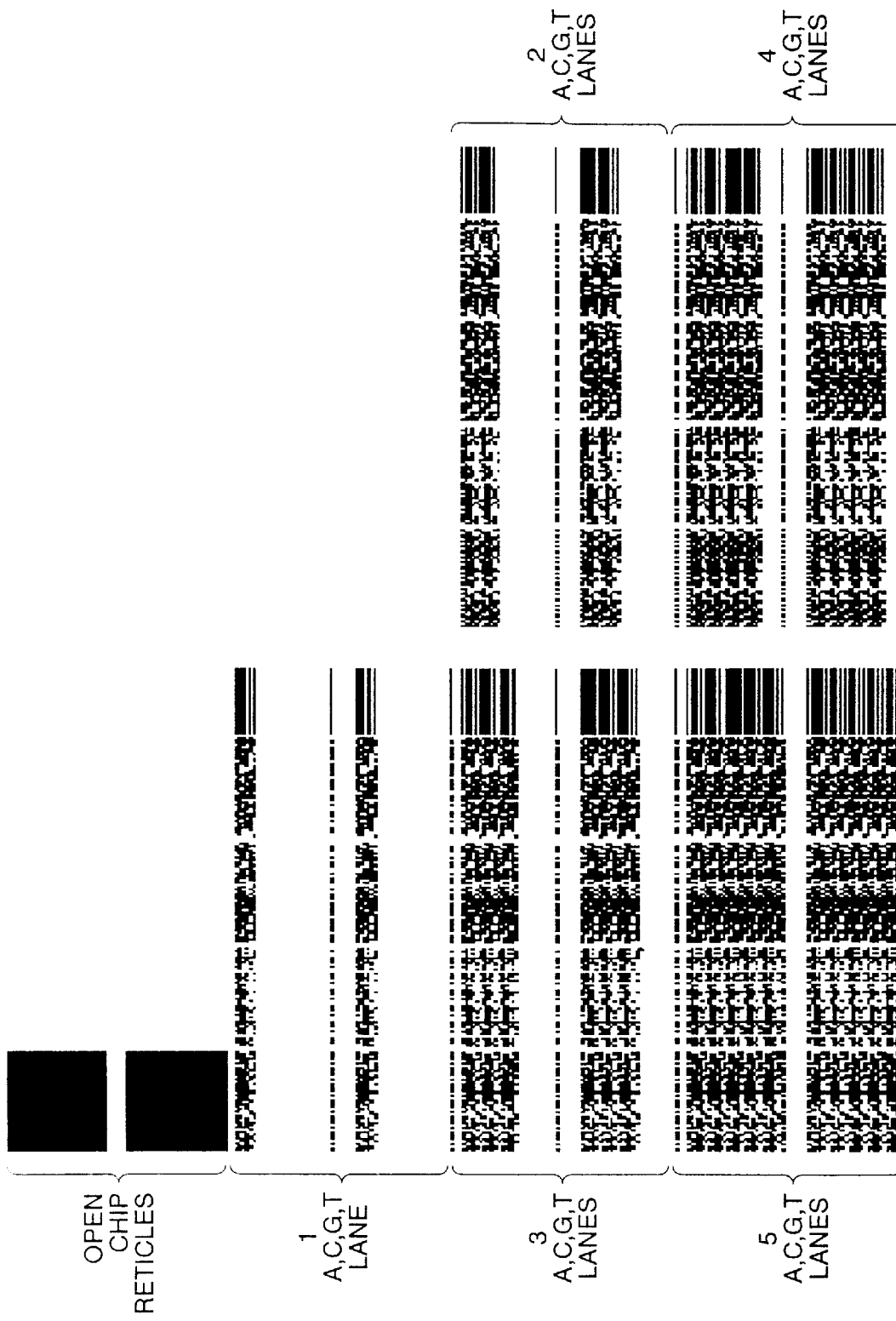
FIG. 14D shows a mask for synthesizing varying length probes on two chips simultaneously.

FIG. 14D shows a mask for synthesizing varying length probes on two chips simultaneously. Ways have been described for utilizing reticles for selecting regions of the chip in order to synthesize probes of varying length (see, e.g., FIGS. 13A and 13B). Another way of achieving this objective is illustrated with the mask in FIG. 14D.

The mask includes reticles similar to the reticles described in FIG. 14C, and in fact, the reticles in the left bottom of the mask are identical to these reticles. The underlying chip has five groups of A, C, G, and T lanes of the chip. As shown, the reticles in the left bottom of the mask have rows of monomer addition regions that correspond to each of the five groups of A, C, G, and T lanes. Each group of A, C, G, and T lanes are identical, however, not all of the reticles have the same number of groups. There are other reticles with one, two, three, and four groups of A, C, G, and T lanes.

In order to synthesize chips with varying length probes, one selects the reticles that will add monomers at desired regions on the chip. For example, if one desires to synthesize 3, 5, 7, 9, and 11-mer probes on two chips simultaneously with interrogation positions at the center of the probes, one could first use the reticles with the single group of A, C, G, and T lanes for one synthesis cycle. This would couple monomers on the top portion of the chip.

Next, one could use the reticles with the two groups of A, C, G, and T lanes for one synthesis cycle. This would synthesize a top region with two layers of monomers (i.e., 2-mer probes) and an adjacent region with one layer of monomers. This process may be repeated utilizing the reticles with three, four and five groups of A, C, G, and T lanes until there are regions on the chip with five, four, three, two and one layer monomers (from top to bottom of the chip).

The interrogation position reticle at the lower middle of the mask may then be utilized to add interrogation position nucleotides to all of the probes on the chip. After the interrogation position reticle has been utilized, the previous process of adding nucleotides may be reversed. After synthesis, open chip reticles may be utilized to cap the probes thereby generating two chips with 3, 5, 7, 9, and 11-mer probes with interrogation positions at the center of the probes. The layout of one of these chips is shown in FIG. 14E.

Figure 15A:
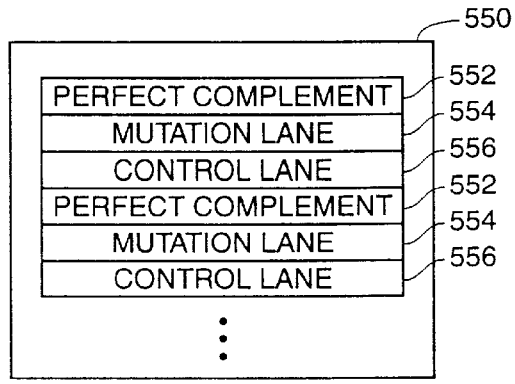
FIG. 15A shows a layout of a chip in another embodiment.

FIG. 15A shows a layout of a chip in another embodiment which is typically utilized for genotyping or gene expression applications. As shown in FIG. 15A, a chip 550 has perfect complement lanes 552, mutation lanes 554 and control lanes 556. The perfect complement lane has probes that are perfectly complementary to the target sequence. The mutation lane has probes that are complementary to the target sequence except for a mutation position. The mutation lanes are utilized to check the validity of the data. Thus, hybridization intensities in the perfect complement lane are compared to the hybridization intensities in the mutation lane.

Figure 15B:
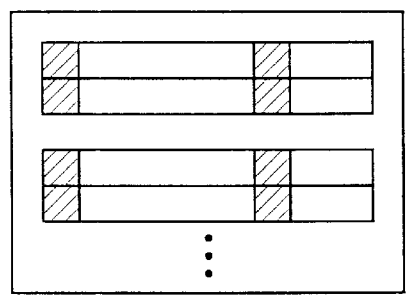
FIG. 15B shows a shift reticle for coupling a particular monomer on a chip in pairs of rows.

FIG. 15B shows a shift reticle for coupling a particular monomer on a chip in pairs of rows. The reticle may be utilized to add nucleotides to both the perfect complement and mutation rows. Typically, there will be four reticles, one for each nucleotide (see, e.g., FIG. 7), that are used in each synthesis cycle. However, only one reticle is shown.

Figure 15C:
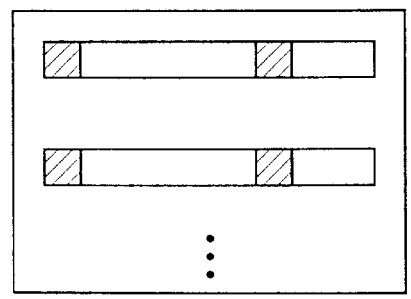
FIG. 15C shows a shift reticle for coupling a particular monomer on a chip in a single lane.

FIG. 15C shows a shift reticle for coupling a particular monomer on a chip in a single lane. In order to produce probes in the mutation lane that differ from the probes in the perfect complement, a shift reticle as shown in FIG. 15C may be utilized. As before, there will typically be four reticles, one for adding each of the nucleotides, but one is shown for simplicity. In one synthesis cycle, these shift reticles may be utilized to add nucleotides that are perfectly complementary to the target sequence in the perfect complement lane as was done with the reticle shown in FIG. 15B.

With the invention, the same shift reticle shown in FIG. 15C may be utilized to add mutation nucleotides to the probes in the mutation lanes. The shift reticles are shifted vertically so that the monomer addition regions overly the mutation lanes. In order to add mutation nucleotides to the probes in the mutation lanes, one may change the order of the nucleotide addition steps in the synthesis cycle. For example, if the nucleotides A, C, G, and then T are added in a synthesis cycle, one can instead add T, G, C, and then A, which is reverse order. Thus, each probe in the mutation lanes will have a mutation nucleotide added.

Alternatively, one may keep the order of the nucleotide addition steps but switch the order of the shift reticles that are utilized. As should be apparent, this has the same effect of adding a mutation nucleotide to the probes in the mutation lanes.

Figure 15D:
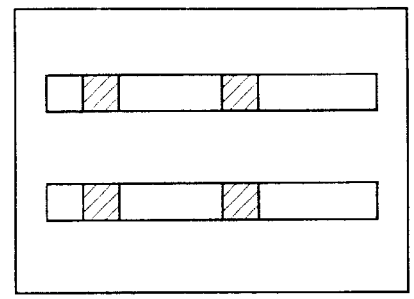
FIG. 15D shows a shift reticle for forming control lanes.

FIG. 15D shows a shift reticle for forming control lanes that include control probes. The control probes may be perfectly complementary to a known oligonucleotide that is hybridized with the chip in order to aid in analyzing the scanning results. Again, one shift reticle is shown but there will typically be one for each monomer.

The above embodiment provides shift reticles which may be utilized to form probes of varying lengths which are complementary to the target sequence. These shift reticles may be utilized with one or more masks in order to produce probes with interrogation position nucleotides or probes of varying length on the same substrate as described. The cost for producing probes on a substrate are reduced because the number of reticles may be greatly reduced (e.g., down to five reticles or less). Flexibility is increased as one may specify characteristics of the probes at synthesis time.

Single Shift Reticle

Figure 16:
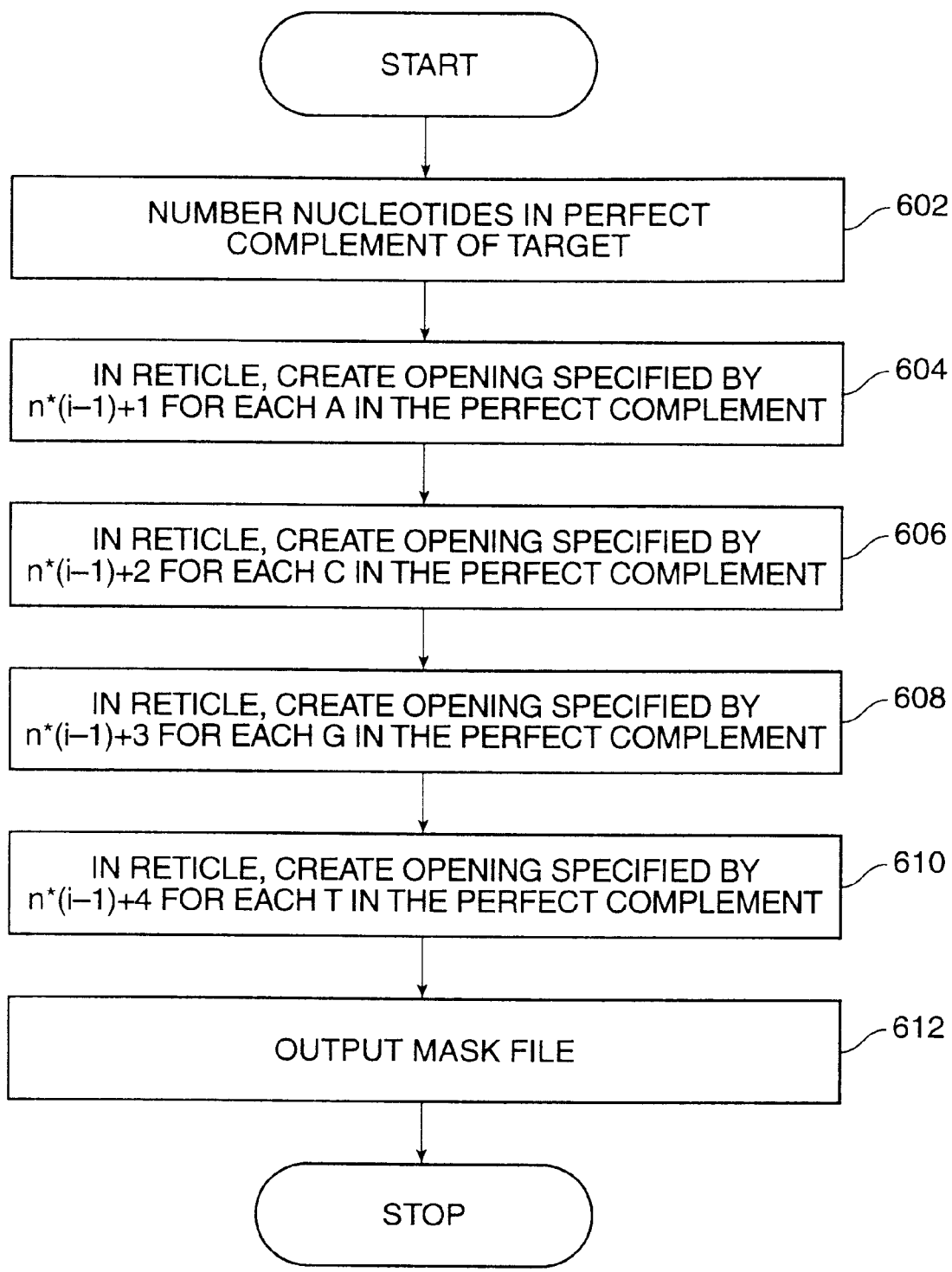
FIG. 16 shows a high level flow of a process of generating reticles according to another embodiment of the present invention.

In another embodiment, the present invention provides a single shift reticle that may be utilized to synthesize probes complementary to the target sequence. FIG. 16 shows a high level flow of a process of generating reticles according to this embodiment of the invention. At step 602, the nucleotides in the perfect complement of the target sequence are numbered. If the target sequence is TGACAT as shown in FIG. 3A, the perfect complement will be ACTGTA. Thus, the nucleotides in the perfect complement are numbered 1–6 with the first A being 1, C being 2, the first T being 3, and so forth.

A single shift reticle is then produced according to steps 604–610. It should be noted that these steps do not need to be performed in any specific order and in fact, they may be performed in parallel. Furthermore, each equation is not specific to the nucleotide shown. However, the steps will be described as being performed sequentially for each nucleotide A, C, G, and T for ease of illustration.

Figure 17A:
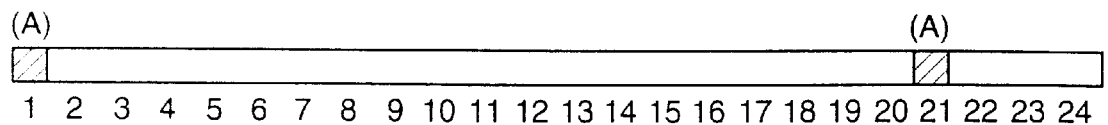
FIGS. 17A–17D show the formation of a single shift reticle.

At step 604, openings are created in the single reticle for each A in the perfect complement by the equation $n*(i-1)+1$, where n is equal to the number of different types of monomers (e.g., nucleotides) and i is equal to a position of the monomer in the perfect complement (or desired probe). As the nucleotide A is at base positions 1 and 6 in the perfect complement, openings will be created in the single reticle at position 1 and 21 because n is equal to 4 for the four nucleotides A, C, G, and T, and i is equal to 1 for the first A and 6 for the second A. FIG. 17A shows the resulting single reticle.

Figure 17B:
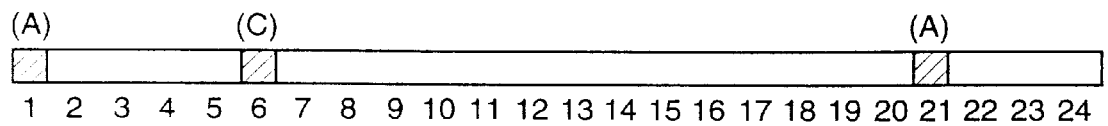

At step 606, openings are created in the single reticle for each C in the perfect complement by the equation $n*(i-1)+2$, where n is equal to the number of different types of monomers and i is equal to a position of the monomer in the perfect complement. As the nucleotide C is at base position 2 in the perfect complement, an opening will be created in the single reticle at position 6 because n is equal to 4 and i is equal to 2. FIG. 17B shows the single reticle with openings for both A and C.

Openings are created in the single reticle for each G in the perfect complement by the equation $n*(i-1)+3$ at step 608.

Figure 17C:
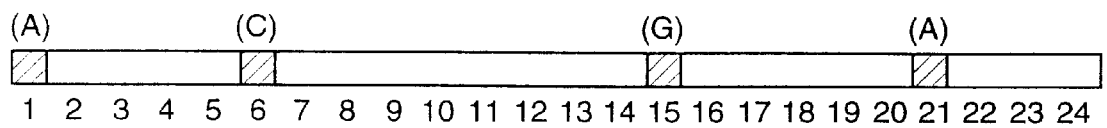

As the nucleotide G is at base position 4 in the perfect complement, an opening will be created in the single reticle at position 15 because n is equal to 4 and i is equal to 2. FIG. 17C shows the single reticle with openings for A, C and G.

Figure 17D:
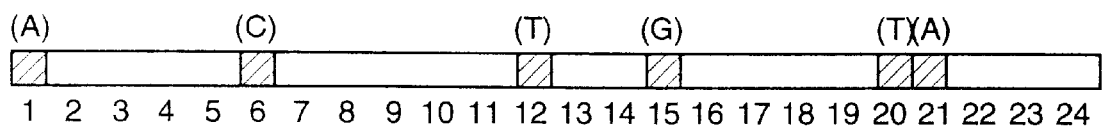

At step 610, openings are created in the single reticle for each T in the perfect complement by the equation $n*(i-1)+4$. As the nucleotide T is at base positions 3 and 5 in the perfect complement, openings will be created in the single reticle at positions 12 and 20 because n is equal to 4 and i is equal to 2. FIG. 17D shows the single reticle with openings for A, C, G, and T.

At step 612, a mask file for generating a mask including the single reticle is output. This mask file is typically utilized by a computer operated system to generate the mask.

Figure 18:
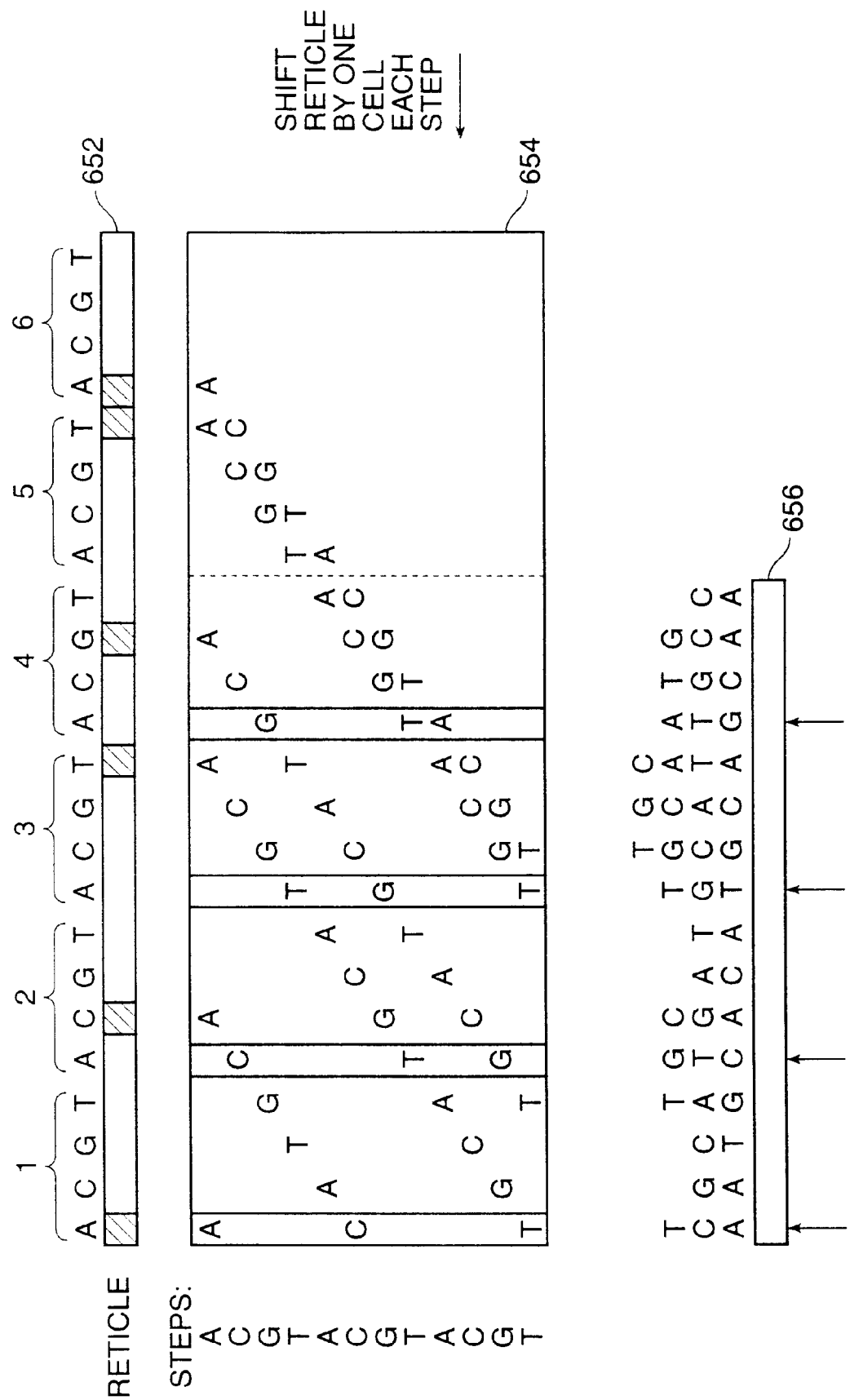
FIG. 18 shows a single reticle that produces the probe set of FIG. 3A and the addition of monomers using this reticle.

FIG. 18 shows a single shift reticle that produces the probe set of FIG. 3A and the addition of monomers using this reticle. Reticle 652 is produced according to the process described in reference to FIG. 16. As shown, the reticle includes six cycles of A, C, G, and T (denoted 1–6 above the reticle). Each cycle includes a single opening at various positions as shown.

Initially, the mask is utilized to add the nucleotide A to the substrate at the regions specified by the mask. With each subsequent synthesis step, the reticle is shifted by one position or cell with each step, resulting in four shifts for each synthesis cycle of nucleotides. This process is shown in a table 654 underneath the reticle with the nucleotide addition steps sequentially listed on the left side of the table. The dashed line in the table represents the rightmost border of the active region of the substrate. In other words, nucleotides to the right of the dashed line would not be coupled to the substrate.

The table is typically not utilized during synthesis but is shown to aid in understanding how the probes on the substrate in this embodiment are formed. Each column in the table represents a probe on the substrate. However, as the table grows downward as monomers are added, the first nucleotide from the top in each column is nearer the substrate.

A substrate 656 results with the desired 3-mer probes indicated by the four arrows underneath the substrate. The desired probes are formed by a uniform addition of nucleotides at these specified regions because each cycle adds one nucleotide to each desired probe. Accordingly, an interrogation position reticle may be utilized that is similar to the ones shown in FIG. 11A and 12A in order to add interrogation position nucleotides. After the interrogation position nucleotides are added, a synthesis cycle of the single shift reticle is then skipped so the reticle is shifted four positions or cells (e.g., to the left in FIG. 18).

Figure 19:
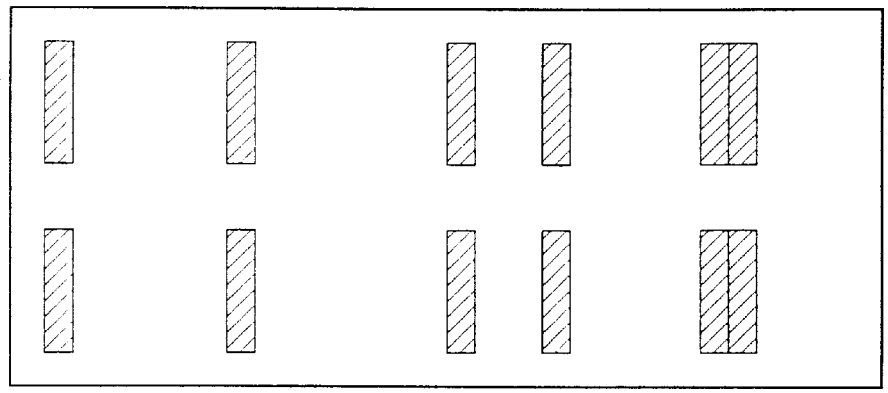
FIG. 19 shows a reticle for producing multiple probe sets.

As shown, there are a number of "junk" probes surrounding the desired probes. Typically these probes will be ignored during sequencing of the target. For simplicity, the single reticle has been shown as a linear reticle. However, a reticle may be utilized for producing two sets of four rows of probes as shown in FIG. 19. More rows of probes may be generated by an extension of the principles of the invention.

Although the single shift reticle has been shown as a long linear reticle, the linear reticle may be transformed into a rectangular shift reticle as shown in FIG. 10. As the single shift reticle is shifted with each monomer addition step, the number of extra cells at the end of each row in the resulting rectangular reticle may be substantially higher.

This embodiment of the present invention allows probes perfectly complementary to the target sequence to be synthesized on the substrate with a single shift reticle. Additional reticles may be utilized to synthesize probes with interrogation position nucleotides or probes of varying lengths as described above. By reducing the number of reticles needed down to possibly one, this embodiment greatly reduces the cost of generating masks for probe array synthesis. Additionally, flexibility is increased because characteristics of the desired probes may be specified at synthesis time.

Other Shift Reticle Embodiments

In another embodiment, the present invention provides shift reticles that may be utilized to synthesize probes for detecting mutations, deletions, and the like. These shift reticles are not target sequence structure specific so the target sequence may be specified at synthesis time. In other words, a set of "generic" shift reticles may be utilized to synthesize probes for analyzing any target sequence. Additionally, these probes may be generated with very few reticles.

FIGS. 20A–20D show shift reticles for synthesizing probes of including multiple monomers for detecting mutations and a deletion. In order to illustrate how the shift reticles work it may be beneficial to discuss an example. Suppose it is desired to synthesize probes that would detect a mutation or deletion at the middle (or 8th) position in a 15-mer target. It should be understood that typically target sequences are much longer but this example will be utilized to illustrate the invention.

If the target sequence is TACCGTGAAGCTACG (SEQ ID NO:1) then it would be desirable to synthesize the following probes: ATGGCAC$\underline{T}$TCGATGC, (SEQ ID NO:2) ATGGCAC$\underline{G}$TCGATGC, (SEQ ID NO:3) ATGGCAC$\underline{C}$TCGATGC, (SEQ ID NO:4) ATGGCAC$\underline{A}$TCGATGC, (SEQ ID NO:5) and ATGGCACTCGATGC (SEQ ID No:6). The interrogation position nucleotides are underlined which illustrates that the first probe is the perfect complement to the target sequence. The next three probes have a mutation at the interrogation position and the last probe has a deletion at the interrogation position.

Figure 20A:
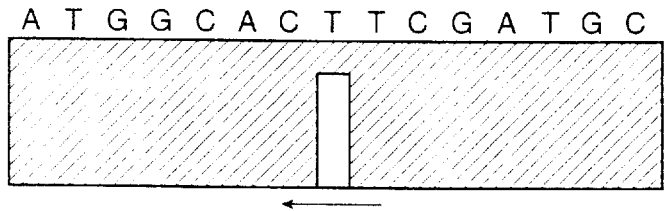
FIG. 20A shows a shift reticle for another embodiment.

Four shift reticles (or less) may be utilized to synthesize these probes. The shift reticle in FIG. 20A is utilized for coupling non-interrogation position monomers to the substrate. Nucleotide addition steps are cycled through that correspond to the complement of the target sequence. As indicated by the nucleotides above the shift reticle, first A is added, then T, then G, and so forth. After each monomer addition step, the shift reticle is shifted one position to the left. As the shift reticle is shown as being five rows high, five identical probes will be generated up to the 8th monomer addition step.

At the 8th monomer addition step, which corresponds to T in the perfect complement, only one monomer addition region overlies the probes. Accordingly, T will be only added to one of the probes, which is the top probe in the FIG. 20A.

Figure 20B:
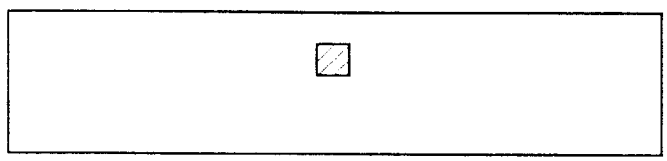
FIGS. 20B–20D shows interrogation position reticles.
Figure 20C:
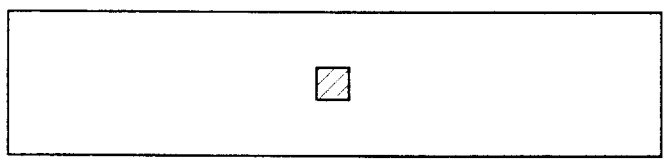
Figure 20D:
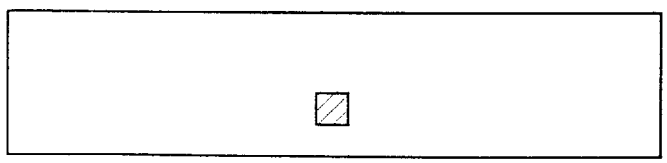

FIG. 20B shows a reticle that has a single monomer addition region. The reticle may be utilized to add a G at the 8th position of the second probe from the top. Similarly, the reticles in FIG. 20C and 20D may be utilized to add a C and A at the 8th position of the probes corresponding to the one monomer addition region of the reticles. The probe at the bottom does not have a monomer added at the 8th position so that a deletion at this position may be detected. Although FIGS. 20B–20D show three shift reticles, a single shift reticle may be utilized that is shifted vertically.

Figure 20E:
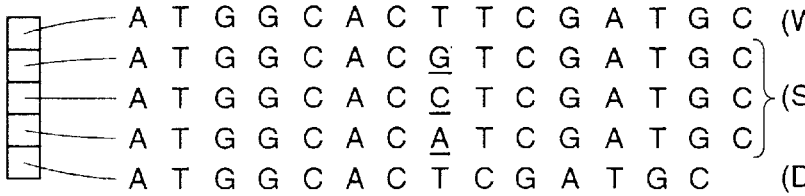
FIG. 20E shows a chip including perfectly complementary, interrogation position and deletion probes.

After the interrogation position nucleotides are added, the shift reticle of FIG. 20A is utilized to add the rest of the nucleotides to the probes. FIG. 20E shows a chip including these probes. A chip 800 includes a perfectly complementary probe, interrogation position probes, and a probe for a deletion (SEQ ID NO:2, SEQ ID NO:3, SEQ ID NO:4, SEQ ID NO:5, and SEQ ID NO:6).

Figure 21A:
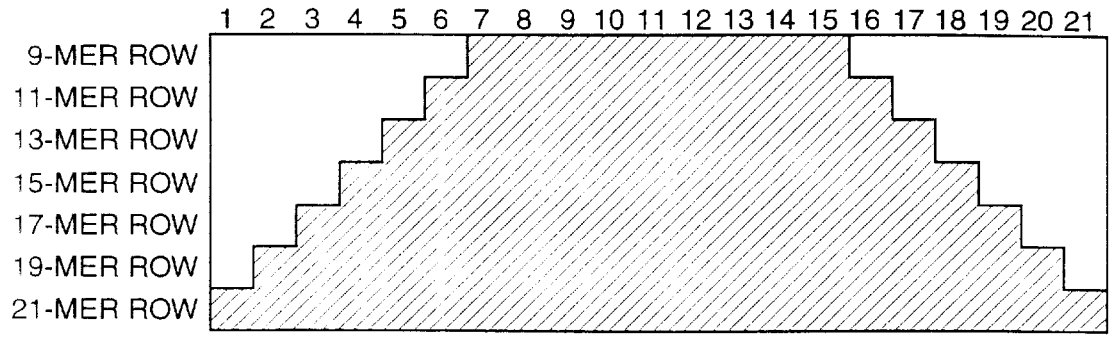
FIG. 21A shows a shift reticle for synthesizing related probes of varying lengths and FIG. 21B shows an example of the layout of the probes that may be synthesized on the substrate.

The shift reticle described above may be modified to produce probes of varying lengths. FIG. 21A shows a shift reticle for synthesizing related probes of varying lengths on a substrate. The shift reticle has monomer addition regions that vary in width to produce 9, 11, 13 15, 17, 19, and 21-mer probes. As the shift reticle is shifted along the direction indicated by the arrow in FIG. 21A, monomers are added to the substrate.

The varying widths of the monomer addition regions may be designed to result in varying length probes that are centered around the same position of a target sequence. For example, as shown in FIG. 21A, each monomer addition step is labeled from 1–21. At step 1, only one region will have a monomer added. Each subsequent step adds a monomer to this region and the region above it. In this way, the stair-step design of the shift reticle allows varying length probes to be synthesized on the substrate. By utilizing a stair-step design at each end of the shift reticle, the probes vary by two monomers instead of one which would be achieved with a single stair-step.

Figure 21B:
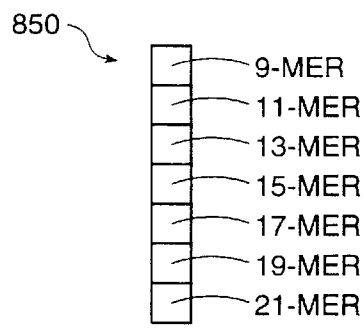

FIG. 21B shows an example of the layout of the probes that may be synthesized on the substrate. A chip 850 includes regions that include 9, 11, 13, 15, 17, 19, and 21-mer probes. Although it has only been described that there is one row for each length probe, there may be multiple rows for each length probe. For example, there may be four rows for each length probe, one for nucleotide at an interrogation position. At the interrogation position, an interrogation position reticle as was described in reference to FIGS. 11A and 12A may be utilized to add the interrogation position nucleotides instead of utilizing the shift reticle. An advantage of the invention is that the sequence of the probes, the length of the probes, and interrogation position may be selected at synthesis time.

This embodiment of the present invention allows probes of varying lengths and that are centered around a position in the target sequence to be synthesized. The shift reticle may also be utilized with an interrogation position reticle to produce varying length probes that detect mutations.

These embodiments of the invention have the significant advantage that the shift reticles are not target sequence structure specific. Accordingly, the sequence of the target may be specified at synthesis time and a "generic" set of shift reticles utilized to synthesize probes for analyzing the target sequence. As with the other embodiments of the invention, the number of reticles needed is significantly reduced which lowers the cost of producing the chips. Also, flexibility is increased because characteristics (e.g., interrogation position) of the desired probes may be specified at synthesis time.

Speckle Masks

Figure 22:
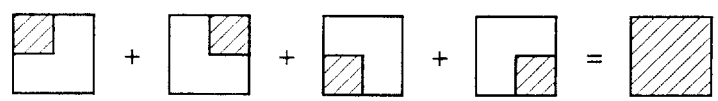
FIG. 22 is a simple example of speckle masks.

Some embodiments of the present invention utilize speckle masks. A "speckle mask" is a set of reticles that when taken together have an opening at each location, thus they, in effect, can be said to form a full open mask. FIG. 22 is a simple example of speckle masks. As shown, the three reticles have a single monomer addition opening at a different location. When the openings are added together, a full open mask is generated. This is a property of speckle masks.

Figure 23:
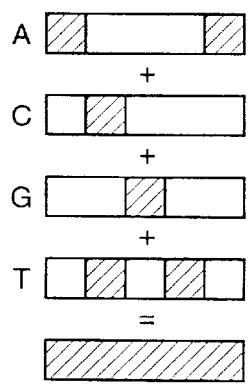
FIG. 23 shows that the shift reticles of FIG. 7 are speckle masks.

Another example of a speckle mask is the set of reticles (or masks) shown in FIG. 7. These masks, together include one and only one opening for each monomer addition region in the reticles. FIG. 23 shows how the openings of the shift reticles add up to form a full open mask.

A fundamental property of speckle masks is that if all the reticles are used in a synthesis cycle, exactly one monomer is added to each of the probes in the active region of the substrate. This property is used to great effect in allowing construction of probes of any length and interrogation position at synthesis time.

Another application of speckle masks is to generate a number of distinct chips from a single speckle set. Take a grid and construct a speckle set by assigning random numbers from 1–4 (or whatever the number of monomers happens to be) in each cell. The number indicates which reticle will have an opening at that location. If all four reticles are cycled through with some permutation of A, C, G, and T in a synthesis cycle, a set of "random" nucleotides are added to each probe on the substrate. If some arbitrary (x and y) offset is utilized in each step, very little correlation between the nucleotides added to each probe is expected. For each distinct set of offsets, radically different sets of probes may be generated. Thus, "random" chips with probes of uniform length (neglecting probes on the edges of the chip) may be generated.

A further application of a speckle set is to generate a chosen set of uniform length probes. A shift mask may be generated that produces a specific set of probes by picking a sequence containing that set of probes, and generating a shift mask to that sequence. However, the sequence containing some set of probes will in general be very much longer than the total number of probes. Since a shift mask contains a number of cells approximating the total length of the sequence, this may be an inefficient way of generating some sets of probes.

A shift mask uses one-dimensional offsets to generate the probes. A way of looking at this is that each probe must be encoded on the mask in a strip 1×n, where n is the length of the probe. The strips are packed onto the mask set to produce the set of probes. Any pair of strips may only interact in $O(n)$ ways, corresponding to the number of ways the rectangles may overlap.

A better method of packing probes onto a speckle set is to use two-dimensional offsets. With 2-dimensional offsets, probes are encoded on the mask in "speckles" some arrangement of n cells (where n is the length of the probe). In general, there are $O(n^2)$ ways for two speckles to interact. This suggests that two-dimensional offsets may be used to pack probes efficiently in a speckle set. However, this problem appears computationally very difficult, given the degrees of freedom to choose offsets, base permutation used at each synthesis cycle, and probe location. Some form of simulated annealing could be used to choose locations, given the chosen set of offsets and base permutation.

Figure 24:
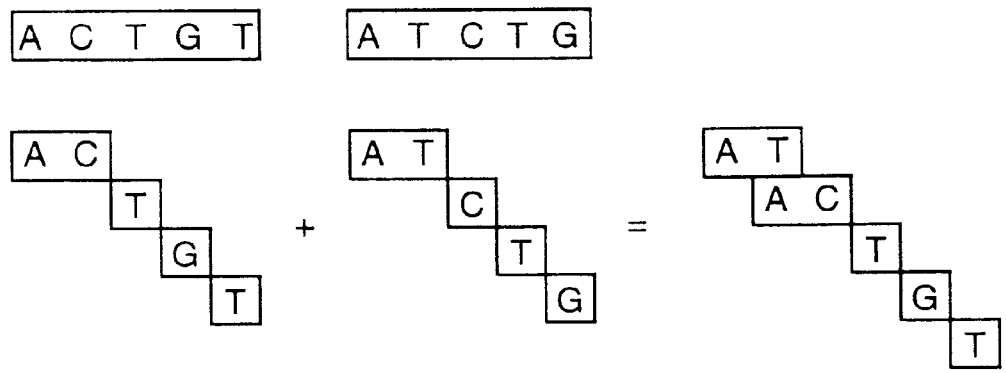
FIG. 24 shows the packing of speckle masks.

FIG. 24 shows the packing of speckle masks. Two sequence ACTGT and ATCTG may be packed by taking advantage of the common subsequence CTG. The packing of the speckle masks involves both an x and y offset as shown.

Several possible generalizations of speckle sets exist. One may use a number of masks greater than the set of bases used to increase the number of degrees of freedom. One may also generate sets of masks that add up to several open masks (each cell is open exactly k times, when the full set of masks is taken together). Additionally, one may generate sets of masks that have many different subsets that add up to an open mask.

Post Chip Synthesis

In the embodiments described above, the reticles were designed as rectangular grids. The rectangular grids are utilized as it lends itself well to switch matrix representation. Switch matrices provide an excellent generalization of combinatorial masks, but they generally require that the chips include an array of rectangular cells, where all of the cells are the same size. These chips may include wasted space as the blank lanes (lanes including no probes) are the same size as lanes which include probes.

With post chip synthesis, each set of related probes (e.g., probes varying by a single base at an interrogation position) are treated as a character in a text document. A set of related probes will be referred to as an "analysis region." Just as characters are not restricted to rectangular grids in modern printers, analysis regions are also not limited but instead may be scaled, rotated, stretched or manipulated. Accordingly, the analysis regions may be input as a sequential list.

Figure 25:
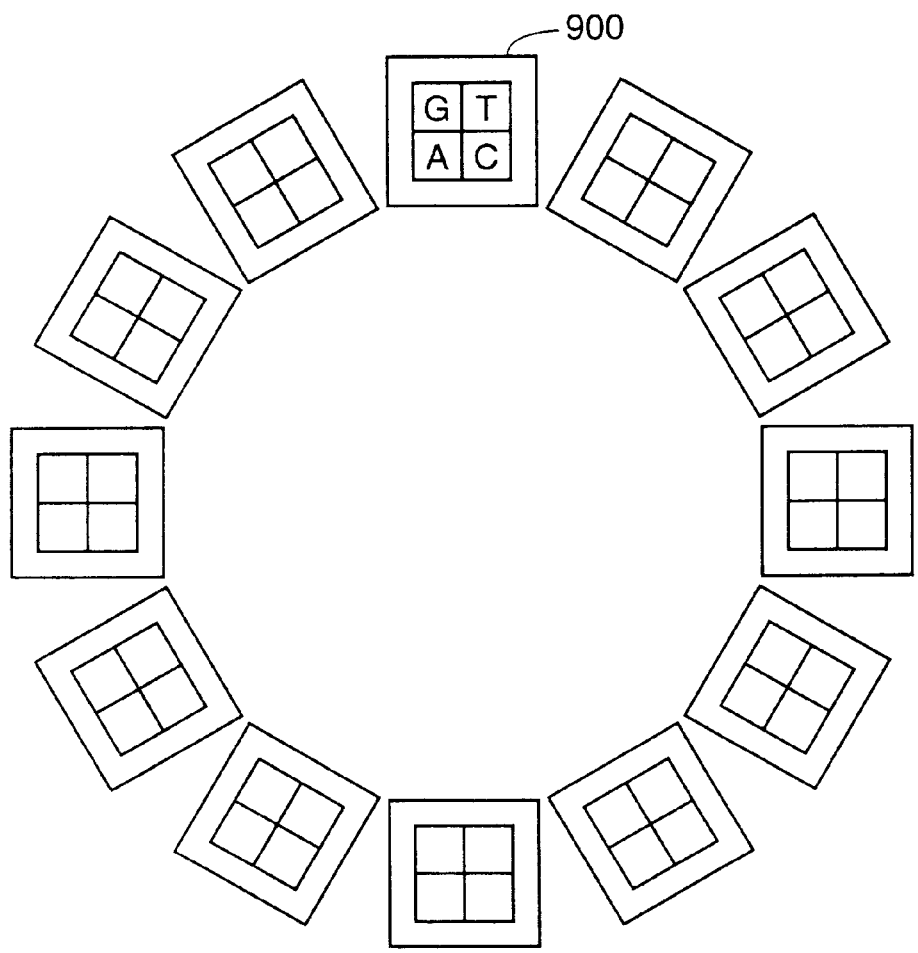
FIG. 25 shows the layout of a chip utilizing post chip synthesis.

FIG. 25 shows the layout of a chip in one post chip synthesis embodiment. An analysis region 900 includes four cells denoted G, T, A, and C to indicate the nucleotide at the interrogation position of the probes in each cell. As shown, the analysis regions are placed in a circular pattern. Although only one ring of analysis regions is shown, more rings may be generated around a center. This pattern of analysis regions may be extended to resemble data that is stored on hard drives, including sectors and tracks, for reading by a computer controlled device.

Figure 26:
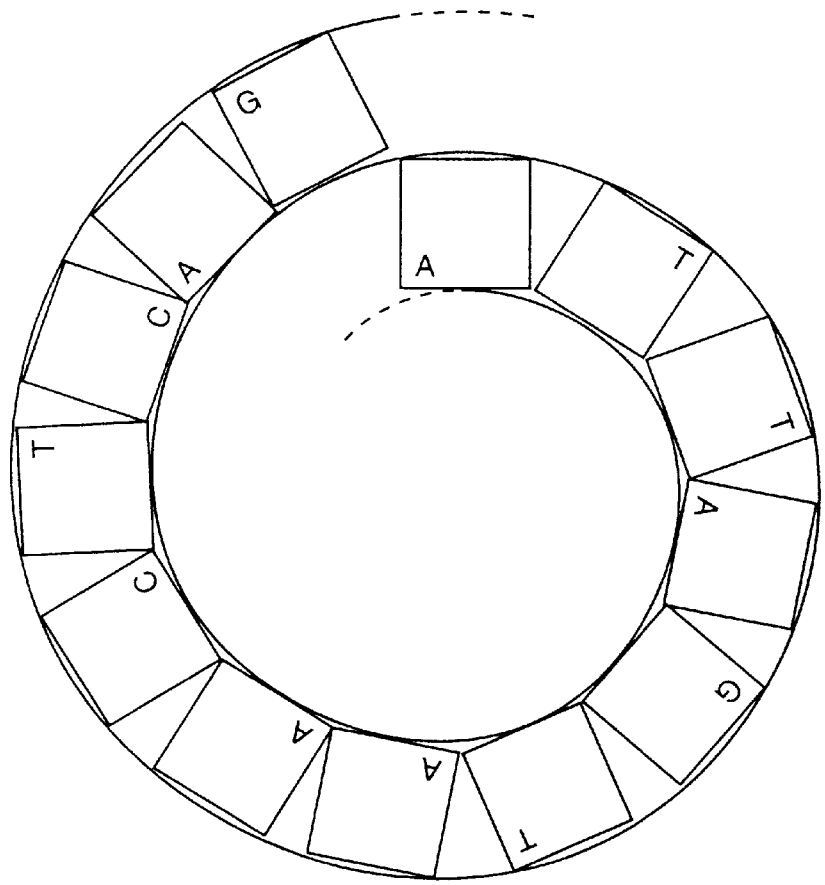
FIG. 26 shows the layout of another chip utilizing post chip synthesis.

FIG. 26 shows the layout of another chip utilizing post chip synthesis. In this embodiment, the analysis regions are synthesized in a spiral pattern, similar to a phonographic record. Additionally, the masks that synthesized the probes on the chips did not add the nucleotides in a rectangular cell. Instead, the probes were synthesized on the chip in an outline of the interrogation nucleotide letter: A, C, G, or T. As expected, the probes that best hybridize with the sample sequence shown generate the highest intensity, which will form the brightest outline of one of these characters. In other words, a person may be able to just read the bases right off the scan image.

Alternatively, a computer system may utilize optical character recognition techniques to read the characters indicative of the interrogation base from the scan image. This process may be further added by the spiral placement of the analysis regions.

With post chip synthesis, analysis regions may be placed in differing orientations, spirals, or with variable spacing between the analysis regions. Flexibility in laying out the chip is provided which may prove to be very beneficial in many applications.

Edge Minimization

Figure 27A:
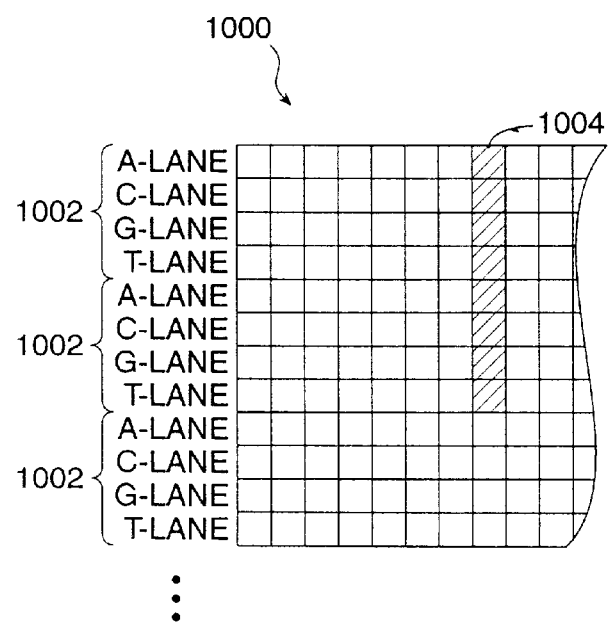
FIG. 27A shows an active region of a chip that has tightly packed lanes.

In order to maximize the utilization of the active region of the substrate, it may be beneficial to pack groups of A, C, G, and T-lanes together with no blank lanes in between. FIG. 27A shows an active region 1000 of a substrate that includes multiple groups of A, C, G, and T-lanes 1002. As shown, there are no blank lanes separating each group of lanes 1002. Although this may appear to be the best utilization of the real estate of the active region, the synthesis of the probes in the T-lane of one group may adversely affect the synthesis of probes in an adjacent A-lane of another group.

Figure 27B:
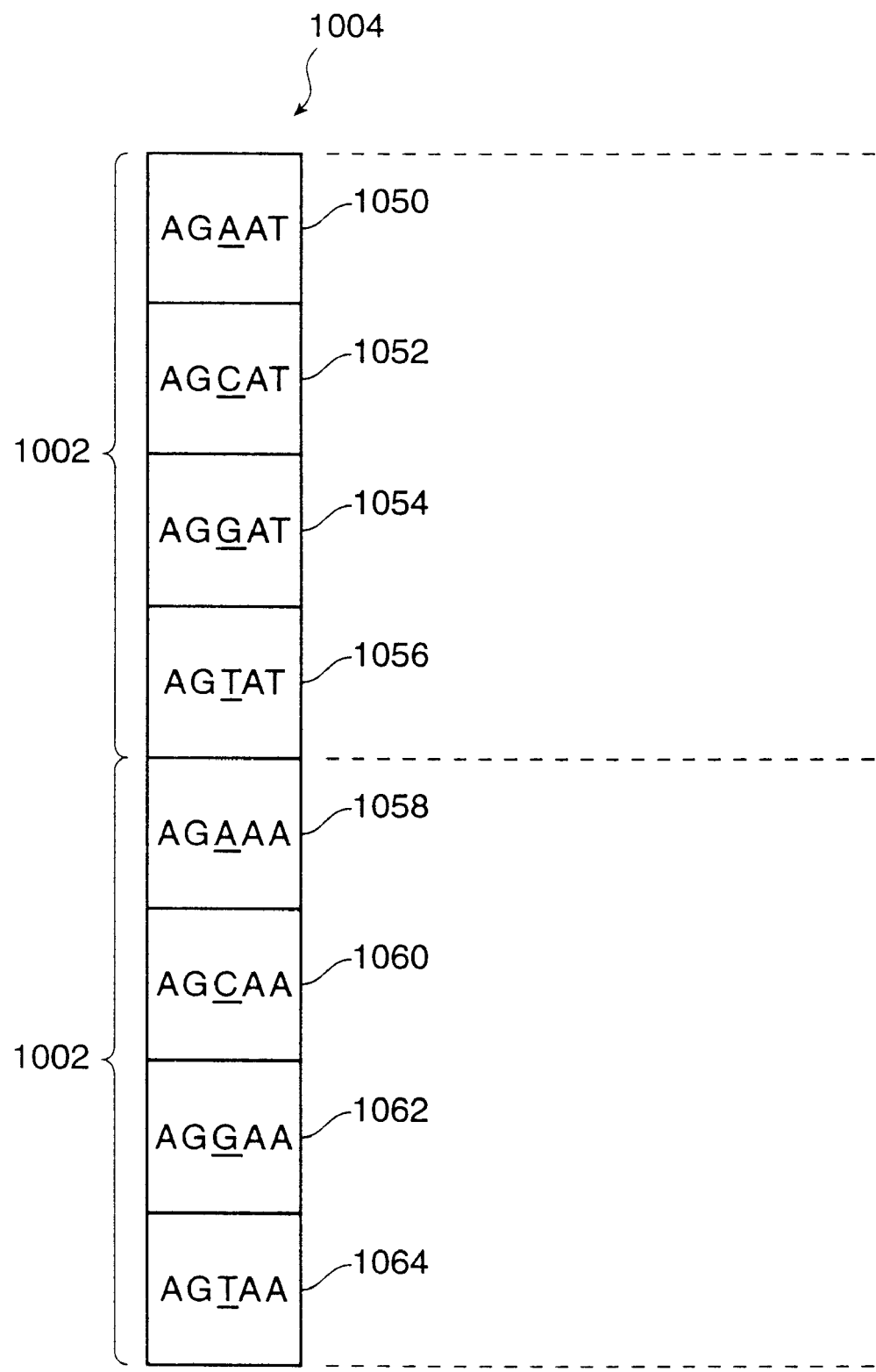
FIG. 27B shows a subregion from FIG. 27A.

In order to show how the synthesis of one group may affect another, FIG. 27B shows a subregion of eight cells 1004 from FIG. 27A. As shown, four of the cells 1050, 1052, 1054, and 1056 are from a first group of A, C, G, and T-lanes and four cells 1058, 1060, 1062, and 1064 are from an adjacent group. Within each cell are 5-mer probes with an interrogation position at the third position (underlined). In practice, the probes are typically longer than 5-mers but shorter probes are shown to benefit the reader.

When the cells on the substrate are tightly packed, data from cells (e.g., cells 1056 and 1058) that are adjacent to another group of cells is not as accurate. The reason for this is that the probe AGTAT from cell 1056 and the probe GCAAA from cell 1058 only have one base in common, the fourth base in both probes is an A. Therefore, during synthesis, many of the masks will have an opening for only one of these cells, which creates an "edge" on the mask between the two cells. Accordingly, it can be said that there are four edges on the reticles utilized to generate the probes in cells 1058 and 1060.

In stark contrast, the probe AGGAT from cell 1054 and the probe AGTAT from cell 1056 have four bases in common. As these two probes are from the same group of probes, only the interrogation position bases differ. Thus, it can be said that there is only one edge on the reticles utilized to generate the probes in cells 1056 and 1058. The significance of the number of edges is described below.

Light tends to diffuse somewhat around an edge of a reticle so the more edges that are present between two cells, the more it is that the cells will have incorrect probes near the edge. As described above, there were four edges between cells 1056 and 1058, whereas there was only one edge between cells 1054 and 1056. Accordingly, the data from probes near the border between cells 1056 and 1058 will likely be less accurate. Although synthesizing a blank lane between the groups of A, C, G, and T-lanes reduces this "edge effect," the reduction is only approximately one half since there will still be edges for the generation of the blank lane.

The present invention reduces the number of edges by utilizing shift reticles that synthesize non-interrogation position bases in an area that is wider that the area in which interrogation position bases are synthesized. For example, the shift reticles shown in FIGS. 9A and 9B have monomer addition regions that are four cells wide. The monomer addition regions may be widened to five cells wide so that non-interrogation position bases are synthesized in an area on the chip that is five cells wide. An interrogation shift reticle, such as shown in FIGS. 11A and 12A, may then be utilized to synthesize interrogation position reticles in an area that is narrower (e.g., four cells wide) than the area occupied by the non-interrogation position bases.

Figure 27C:
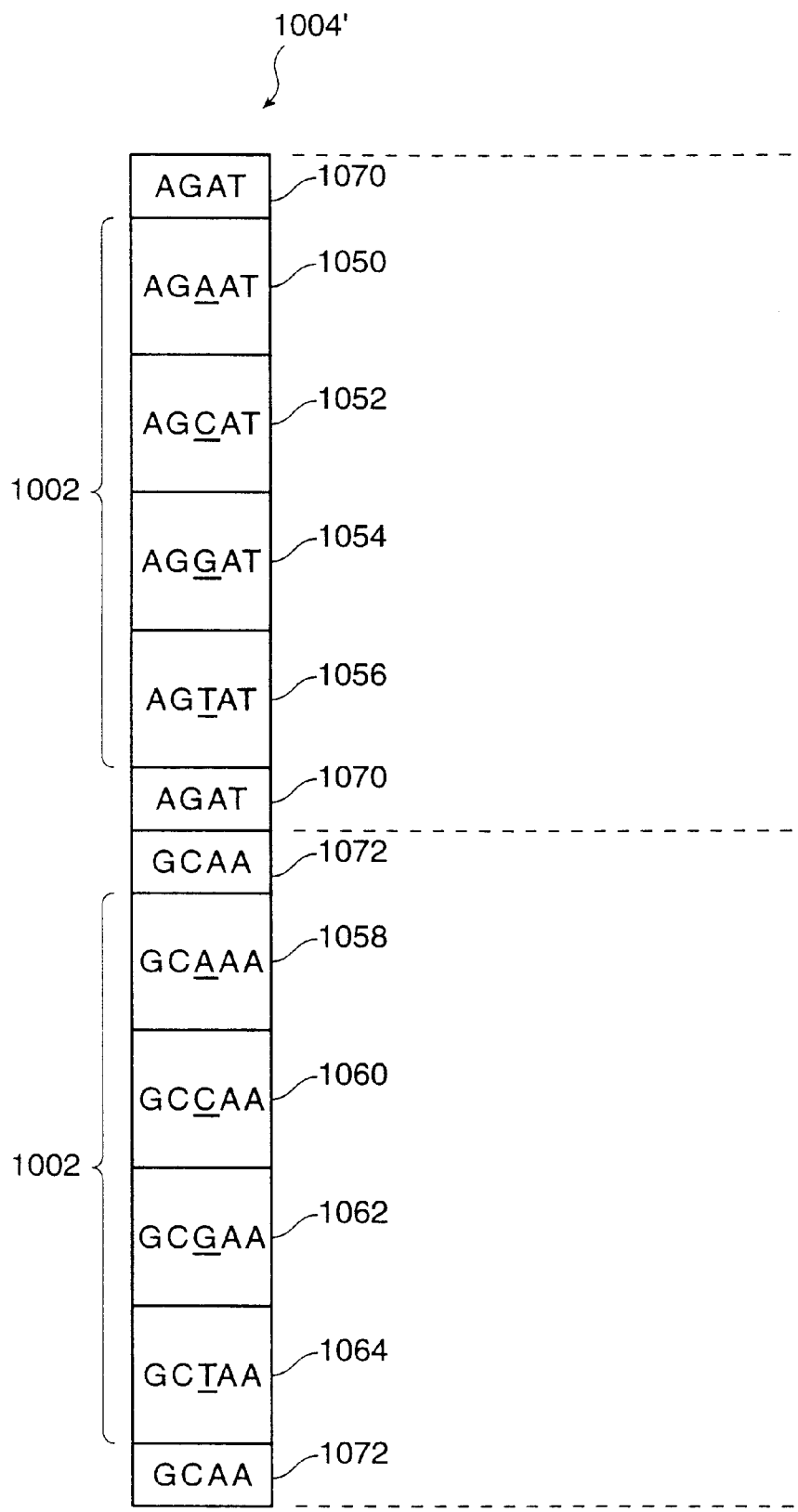
FIG. 27C shows how the subregion of FIG. 27B may be synthesized to minimize edges.

In order to more clearly see how the invention provides a reduction in edges, FIG. 27C shows a subregion of FIG. 27B that may be synthesized with reduced edges. A subregion 1004' includes eight cells 1050, 1052, 1054, 1056, 1058, 1060, 1062, and 1064 that are the same as those in FIG. 27B that have the same reference numerals. However, in subregion 1004, the non-interrogation position bases are synthesized five cells wide. Accordingly, there are half cells 1070 and 1072 surrounding each of the multiple groups of A, C, G, and T-lanes 1002.

Half cells 1070 include the same bases as the probes in cells 1050 and 1056 except for a single additional base, the interrogation base. Therefore, there is only one edge difference between half cells 1070 and the full cells they border. As described above, there is only a one edge difference between, e.g., cells 1054 and 1056. Therefore, each of cells 1050, 1052, 1054, and 1056 have the same number of edges at their borders so they should provide more accurate data.

Although in preferred embodiments, the non-interrogation position bases are synthesized in an area five cells wide, this exact size is not required. Edges may be reduced when the non-interrogation position bases are synthesized in an area that is wider than the area in which the interrogation position bases are synthesized. It may seem that having unused space between groups of lanes would waste real estate in the active area on the chip. However, it has been found that because the data is more accurate, the feature sizes may be reduced more so that the density of cells may actually be increased.

Probe Optimization

In some instances, it may be beneficial to synthesize various probes that interrogate a specific base position in a target. For example, one may only be interested in specific point mutations in a gene. In order to fully interrogate the specific base, it would be beneficial to have many different probes (e.g., length and/or interrogation position in the probe) that interrogate the position.

Figure 28:
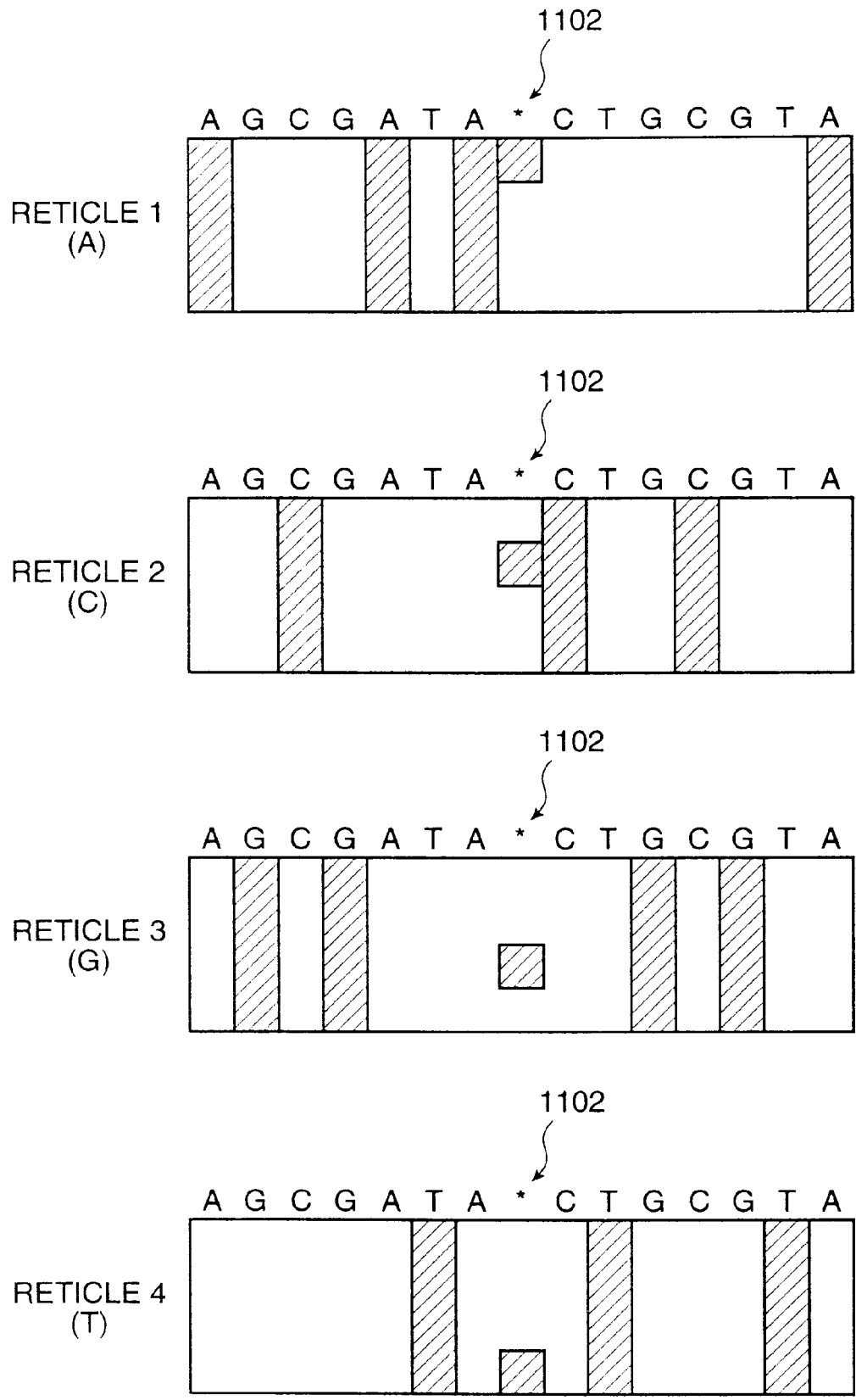
FIG. 28 shows shift reticles that produce equal length probes with different interrogation positions.

An embodiment of the invention allows one to synthesize different probes for interrogating a specific base position. Conceptually, the invention combines the non-interrogation base reticles with the interrogation position reticle. FIG. 28 shows shift reticles that produce equal length probes with different interrogation positions. It should be understood that in this instance, "interrogation position" means the position in the probe that interrogates a position in the target. The "interrogation position" may also refer to the position in the target that is being interrogated.

Assume a target was AGCGATA<u>N</u>CTGCGTA, (SEQ ID NO:7) where the underlined N designates an unknown base at an interrogation position. The shift reticles of FIG. 28 may be created as described in reference to FIG. 7. The bases shown on top of the shift reticles are merely a reference to the corresponding base in the target and an asterisk 1102 indicates the interrogation position. The cells at this location in the reticles will be formed similar to the interrogation position reticles of FIG. 11A or 12A. As shown, at the interrogation position, a different monomer addition region is generated for each reticle. For example, Reticle 1 (for A) has a monomer addition region in the A-lane, Reticle 2 (for C) has a monomer addition region in the C-lane, and so forth.

When the shift reticles of FIG. 28 are utilized, there is no need for an interrogation position reticle. After eight cycles through the addition of A, C, G, and T with the shift reticles, 8-mer probes would be synthesized that have all the possible interrogation positions in the probes.

Figure 29:
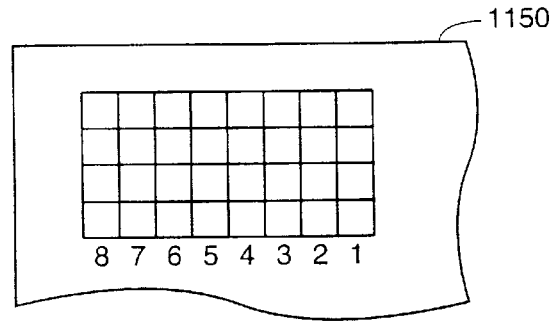
FIG. 29 illustrates the probes that may be produced by the reticles of FIG. 28.

FIG. 29 illustrates an example of the position of the 8-mer probes. A chip 1150 has eight different sets of four probes in its active region. The number below (1–8) indicates the position of the interrogation position in the probes if the shift reticles of FIG. 28 are shifted to the left after each monomer addition step. A "1" indicates that interrogation position is nearer the chip in the probes, whereas an "8" indicates that the interrogation position is farther from the chip in the probes.

By utilizing the shift masks in FIG. 28, one may synthesize probes of a specific length with every possible interrogation position. Although 8-mers have been described as an example, the invention is not limited to any specific probe length. Additionally, probes may be further optimized by having probes of different lengths synthesized on the chip at the same time as follows.

Figure 30:
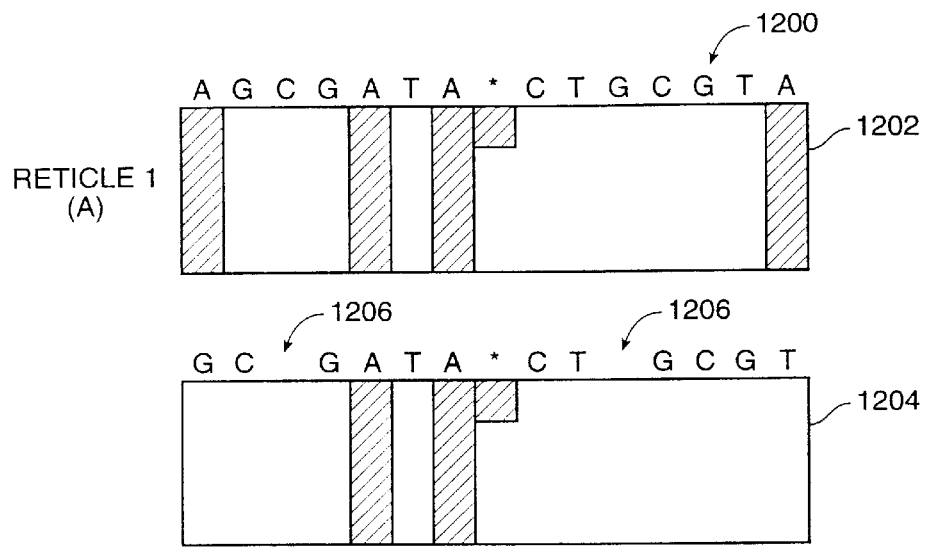
FIG. 30 shows a shift reticle for producing probes with different lengths and interrogation positions.

FIG. 30 shows a shift reticle 1200 for producing probes with different lengths and interrogation positions. The top half of the shift reticle 1202 is the same as Reticle 1 of FIG. 28. Accordingly, it may be utilized to form 8-mer probes with different interrogation positions. The bottom half of the shift reticle 1204 is similar to the top half except that it has two "blank" positions 1206. These blank positions will not have any monomer addition regions in any of the shift reticles. Because there are two base positions that are blank, the bottom half of the shift reticle does not cover as much of the target as the top half. For simplicity, only one shift reticle is shown but it should be readily understood that for nucleic acid applications, there will be three other shift reticles for the other three bases.

Figure 31:
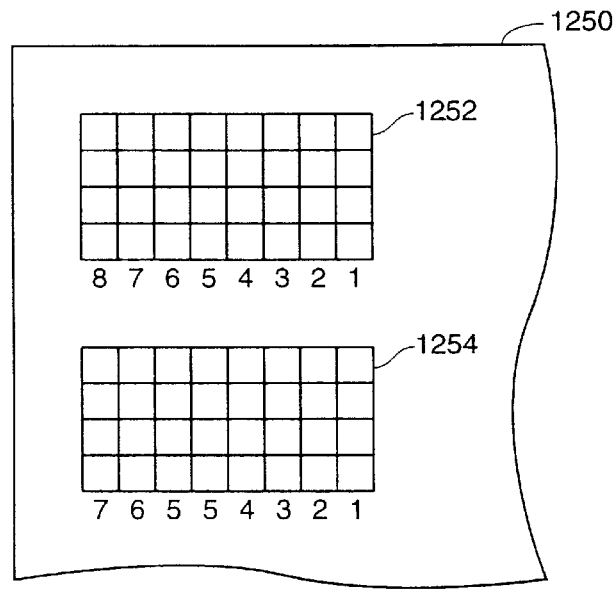
FIG. 31 illustrates the probes that may be produced by the shift reticles according to FIG. 30.

FIG. 31. illustrates the probes that may be produced by shift reticles according to FIG. 30. A chip 1250 has two probe regions corresponding to the different halves of the shift reticle of FIG. 30. A first region 1252 has eight different sets of four probes where the number below (1–8) indicates the position of the interrogation position in the probes. As before, a "1" indicates that interrogation position is nearer the chip in the probes, whereas an "8" indicates that the interrogation position is farther from the chip in the probes.

A second region 1254 has eight different sets of four probes, but as indicated by the number below (1–7), there are two sets of probes with an interrogation position at the fifth base in the probes. The duplicate set of probes was generated because of a blank position in the shift reticle. Additionally, the probes in region 1254 will be 7-mers and include probes with interrogation positions at each possible position in the probes. Therefore, probes of different lengths and different interrogation positions may be synthesized on a chip at the same time with an embodiment of the shift reticles of the invention.

The formation of duplicate sets of probes may be also utilized to isolate problems during synthesis and/or to increase the accuracy of the resulting data. For example, although the two sets of probes in region 1254 that have an interrogation position at the fifth base may be identical in terms of sequence, the bases were synthesized during different monomer addition steps. Accordingly, if the fourth monomer addition step that adds an A is faulty, this may affect one set of probes but not the other. Therefore, by analyzing the accuracy of the data from the duplicate set of probes, one can identify synthesis problems and since there may be duplicate sets of probes, the synthesis problems may be accounted for by utilizing another probe set.

In some embodiments, blank probes are placed in the shift reticles at various locations so that duplicate probe sets will be formed. As discussed above, the duplicate probe sets may be utilized to isolate problems during synthesis and possibly even accounting for the errors.

Figure 32:
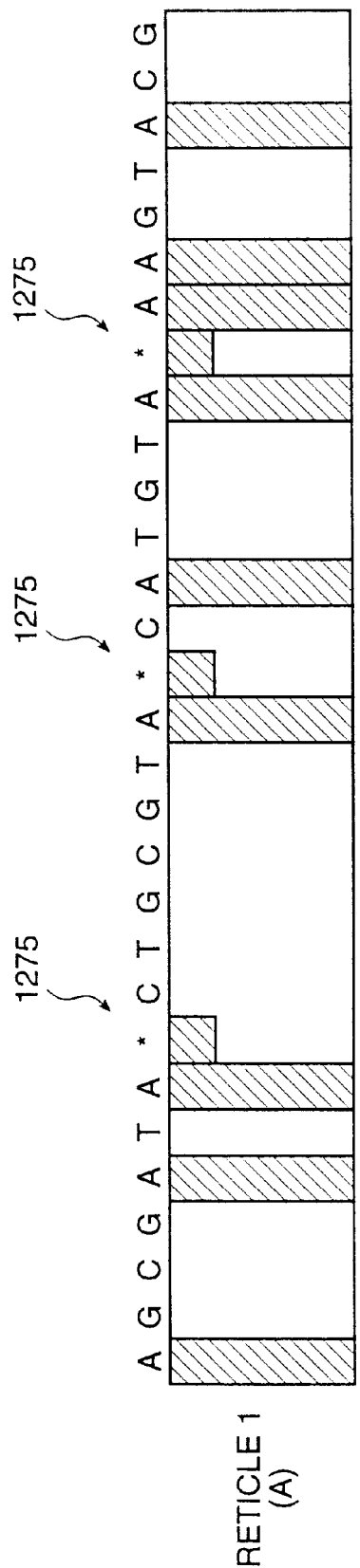
FIG. 32 shows a shift reticle for producing probes that interrogate every ninth base position in a target.

The shift reticles may also be longer to synthesize probes that interrogate multiple base positions in the target. FIG. 32 shows a shift reticle for producing probes that interrogate every ninth base position in the target. The first part of the shift reticle is the same as shown in FIG. 28 (Reticle 1). However, this shift reticle is longer and may be utilized to interrogate the base positions indicated by the asterisks 1275. Probes similar to the one in FIG. 32 may be utilized to form, e.g., 8-mer probes that interrogate every ninth position in the target with probes that have every possible interrogation position. Although the interrogation positions in the target that are being interrogated is fixed in the design of the shift reticles, other shift reticles may be produced to interrogate other positions in the target.

One may also reduce the number of probes by utilizing one set of shift reticles for the even interrogation positions and one set of shift reticles for the odd interrogation positions. Both sets of probes are utilized and then shifted. In this manner, probes that have interrogation positions at every other possible location may be synthesized. Since there are less probes synthesized on the chip, more base positions in the target may be interrogated on the chip. Although two sets of shift reticles have been described (one for even positions and one for odd positions), more sets of shift reticles may be utilized. For example, one may utilize a different set of shift reticles for each base position in the target where (base position mod 3=0), (base position mod 3=1), and (base position mod 3=2).

The above description is illustrative and not restrictive. Many variations of the invention will become apparent to those of skill in the art upon review of this disclosure. Merely by way of example, while the invention is illustrated primarily with regard to the synthesis of oligonucleotide or RNA, the invention will find application to the synthesis of many other molecules. Further, while the invention is primarily illustrated in relation to the fabrication of small numbers of identical arrays, the invention may also be applied to situations where a large number of identical arrays is to be synthesized. The scope of the invention should, therefore, be determined not with reference to the above description, but instead should be determined with reference to the appended claims along with their full scope of equivalents.

---

What is claimed is:

1. A method of synthesizing polymers on a substrate, comprising:

coupling monomers on the substrate at locations specified by a plurality of shift reticles, each shift reticle for adding a specific monomer to the substrate and the monomers are selected from the group consisting of nucleotides, amino acids and saccharides;

shifting the plurality of shift reticles relative to the substrate; and after shifting the plurality of shift reticles, coupling monomers on the substrate at locations specified by the plurality of shift reticles so that polymers are synthesized on the substrate that include monomers.

2. The method of claim 1, further comprising utilizing each of the shift reticles to couple a first layer of different types of monomers on the substrate.

3. The method of claim 2, further comprising shifting each of the shift reticles relative to the substrate in order to couple a second layer of different types of monomers on the substrate.

4. The method of claim 1, wherein each shift reticle has monomer addition regions corresponding to positions of the specific monomer in a target sequence.

5. A method of synthesizing polymers on a substrate, comprising:

coupling monomers on the substrate at locations specified by a shift reticle, wherein the monomers are selected from the group consisting of nucleotides, amino acids and saccharides;

shifting the shift reticle relative to the substrate; and after shifting the shift reticle, coupling monomers on the substrate at locations specified by the shift reticle wherein the shift reticle includes monomer addition regions specified by $$n*(i-1)+1$$

wherein n=the number of different types of monomers and i=a position of a first monomer in a target sequence.

6. The method of claim 5, wherein the shift reticle has monomer addition regions specified by $$n*(i-1)+2$$

wherein n=the number of different types of monomers and i=a position of a second monomer in the target sequence.

7. The method of claim 5, further comprising utilizing the shift reticle to couple a first layer of different types of monomers on the substrate at specified locations.

8. The method of claim 7, further comprising shifting the shift reticle relative to the substrate in order to couple a second layer of different types of monomers on the substrate at the specified locations.

9. The method of claim 1, further comprising:

coupling monomers on the substrate at locations specified by an interrogation position reticle;

shifting the interrogation position reticle relative to the substrate; and after shifting the interrogation position reticle, coupling monomers on the substrate at locations specified by the interrogation position reticle.

10. The method of claim 9, wherein the interrogation position reticle is shifted in a direction perpendicular to a direction that the plurality of shift reticles are shifted.

11. The method of claim 1, wherein the plurality of shift reticles includes a shift reticle with a monomer addition region corresponding to each monomer in desired polymers except for non-wild type interrogation position monomers.

12. The method of claim 11, further comprising shifting the shift reticle relative to the substrate in order to couple each monomer in the desired polymers except for the non-wild type interrogation position monomers.

13. The method of claim 1, wherein the plurality of shift reticles includes a shift reticle with monomer addition regions corresponding to different lengths of desired polymers.

14. The method of claim 13, further comprising shifting the shift reticle relative to the substrate in order to synthesize the desired polymers of different lengths.

15. The method of claim 1, wherein the plurality of shift reticles uniformly adds monomers to the substrate at specified locations after a monomer addition cycle.

16. The method of claim 15, further comprising the step of specifying a characteristic of the polymers desired to be synthesized utilizing the plurality of shift reticles.

17. The method of claim 16, wherein the characteristic of the desired polymers is input at synthesis time.

18. The method of claim 16, wherein the characteristic is a length of the desired polymers.

19. The method of claim 16, wherein the characteristic is an interrogation position of the desired polymers.

20. The method of claim 15, wherein the characteristic is a monomer addition in order for synthesizing the desired polymers.

21. A method of synthesizing polymers on the substrate, comprising:

providing at least one reticle, the at least one reticle for uniformly adding monomers to the substrate at specified locations for each cycle of monomer addition steps, wherein the monomers are selected from the group consisting of nucleotides, amino acids and saccharides;

specifying a characteristic of the polymers desired to be synthesized utilizing the at least one reticle; and synthesizing the desired polymers on the substrate utilizing the at least one reticle.

22. The method of claim 21, wherein the characteristic of the desired polymers is input at synthesis time.

23. The method of claim 21, wherein the characteristic is a length of the desired polymers.

24. The method of claim 21, wherein the characteristic is an interrogation position of the desired polymers.

25. The method of claim 21, wherein the characteristic is a monomer addition order for synthesizing the desired polymers.

* * * * *